United States Patent
Beyar et al.

(10) Patent No.: US 9,642,932 B2
(45) Date of Patent: May 9, 2017

(54) BONE CEMENT AND METHODS OF USE THEREOF

(75) Inventors: Mordechay Beyar, Caesarea (IL); Oren Globerman, Kfar-Shemaryahu (IL)

(73) Assignee: DePuy Synthes Products, Inc., Raynham, MA (US)

( * ) Notice: Subject to any disclaimer, the term of this patent is extended or adjusted under 35 U.S.C. 154(b) by 1046 days.

(21) Appl. No.: 12/377,894

(22) PCT Filed: Sep. 11, 2007

(86) PCT No.: PCT/IL2007/001130
§ 371 (c)(1),
(2), (4) Date: Aug. 3, 2009

(87) PCT Pub. No.: WO2008/032322
PCT Pub. Date: Mar. 20, 2008

(65) Prior Publication Data
US 2010/0168271 A1    Jul. 1, 2010

Related U.S. Application Data

(60) Provisional application No. 60/825,609, filed on Sep. 14, 2006.

(51) Int. Cl.
*A61K 6/08* (2006.01)
*A61L 24/04* (2006.01)
*A61K 6/00* (2006.01)

(52) U.S. Cl.
CPC .......... *A61L 24/046* (2013.01); *A61K 6/0002* (2013.01); *A61L 2400/06* (2013.01); *A61L 2430/02* (2013.01)

(58) Field of Classification Search
CPC .................................................. A61K 6/0002
USPC ........ 523/105, 115, 116; 525/193, 308, 309, 525/937; 623/23.62
See application file for complete search history.

(56) References Cited

U.S. PATENT DOCUMENTS

| | | | |
|---|---|---|---|
| 229,932 A | 7/1880 | Witsil |
| 370,335 A | 9/1887 | Hunter |
| 817,973 A | 4/1906 | Hausman |
| 833,044 A | 10/1906 | Goodhugh |
| 843,587 A | 2/1907 | DePew |
| 1,175,530 A | 3/1916 | Kirchoff |
| 1,612,281 A | 12/1926 | Goetz |

(Continued)

FOREIGN PATENT DOCUMENTS

| AU | 724544 | 11/1996 |
| AU | 9865136 | 9/1998 |

(Continued)

OTHER PUBLICATIONS

US Office Action, from U.S. Appl. No. 11/360,251, mailed Apr. 17, 2009.

(Continued)

*Primary Examiner* — Michael Pepitone
(74) *Attorney, Agent, or Firm* — Nutter McClennen & Fish LLP

(57) ABSTRACT

A bone cement comprising an acrylic polymer mixture which is formulated to have a relatively high viscosity for a relatively long window, due to distributions of molecular weights and/or sizes of acrylic beads.

11 Claims, 5 Drawing Sheets

(56) References Cited

U.S. PATENT DOCUMENTS

| | | |
|---|---|---|
| 1,612,996 A | 1/1927 | Waagbo |
| 1,733,516 A | 10/1929 | Jamison |
| 1,894,274 A | 1/1933 | Jacques |
| 1,929,247 A | 10/1933 | Hein |
| 408,668 A | 4/1934 | Norman et al. |
| 2,123,712 A | 7/1938 | Clark |
| 2,283,915 A | 5/1942 | Cole |
| 2,394,488 A | 2/1946 | Rotter et al. |
| 2,425,867 A | 8/1947 | Davis |
| 2,435,647 A | 2/1948 | Engseth |
| 2,497,762 A | 2/1950 | Davis |
| 2,521,569 A | 9/1950 | Davis |
| 2,567,960 A | 9/1951 | Meyers et al. |
| 2,745,575 A | 5/1956 | Spencer |
| 2,773,500 A | 12/1956 | Young |
| 2,808,239 A | 10/1957 | Alfred |
| 2,874,877 A | 2/1959 | Spencer |
| 2,918,841 A | 12/1959 | Poupitch |
| 2,928,574 A | 3/1960 | Wagner |
| 2,970,773 A | 2/1961 | Horace et al. |
| 3,058,413 A | 11/1962 | Cavalieri |
| 3,063,449 A | 11/1962 | Schultz |
| 3,075,746 A | 1/1963 | Yablonski et al. |
| 3,108,593 A | 10/1963 | Glassman |
| 3,151,847 A | 10/1964 | Broomall |
| 3,198,194 A | 8/1965 | Wilburn |
| 3,216,616 A | 11/1965 | Blankenship, Jr. |
| 3,224,744 A | 12/1965 | Broomall |
| 3,225,760 A | 12/1965 | Di Cosola |
| 3,254,494 A | 6/1966 | Chartouni |
| 3,362,793 A | 1/1968 | Massoubre |
| 3,381,566 A | 5/1968 | Passer |
| 3,426,364 A | 2/1969 | Lumb |
| 3,515,873 A | 6/1970 | Higgins |
| 3,559,956 A | 2/1971 | Gray |
| 3,568,885 A | 3/1971 | Spencer |
| 3,572,556 A | 3/1971 | Pogacar |
| 3,605,745 A | 9/1971 | Hodosh |
| 3,615,240 A | 10/1971 | Sanz |
| 3,674,011 A | 7/1972 | Michel et al. |
| 3,701,350 A | 10/1972 | Guenther |
| 3,750,667 A | 8/1973 | Pshenichny et al. |
| 3,789,727 A | 2/1974 | Moran |
| 3,796,303 A | 3/1974 | Allet-Coche |
| 3,798,982 A | 3/1974 | Lundquist |
| 3,846,846 A | 11/1974 | Fischer |
| 3,850,158 A | 11/1974 | Elias et al. |
| 3,867,728 A | 2/1975 | Stubsted et al. |
| 3,873,008 A | 3/1975 | Jahn |
| 3,875,595 A | 4/1975 | Froning |
| 3,896,504 A | 7/1975 | Fischer |
| 3,901,408 A | 8/1975 | Boden et al. |
| 3,921,858 A | 11/1975 | Bemm |
| 3,931,914 A | 1/1976 | Hosaka et al. |
| 3,942,407 A | 3/1976 | Mortensen |
| 3,976,060 A | 8/1976 | Hildenbrandt et al. |
| 3,993,250 A | 11/1976 | Shure |
| 4,011,602 A | 3/1977 | Rybicki et al. |
| 4,062,274 A | 12/1977 | Knab |
| 4,077,494 A | 3/1978 | Spaude et al. |
| 4,079,917 A | 3/1978 | Popeil |
| 4,090,640 A | 5/1978 | Smith et al. |
| 4,093,576 A | 6/1978 | Dewijn |
| 4,105,145 A | 8/1978 | Capra |
| 4,115,346 A | 9/1978 | Gross et al. |
| 4,146,334 A | 3/1979 | Farrell |
| 4,168,787 A | 9/1979 | Stamper |
| 4,170,990 A | 10/1979 | Baumgart et al. |
| 4,180,070 A | 12/1979 | Genese |
| 4,185,072 A | 1/1980 | Puderbaugh et al. |
| 4,189,065 A | 2/1980 | Herold |
| 4,198,383 A | 4/1980 | Konsetov et al. |
| 4,198,975 A | 4/1980 | Haller |
| 4,204,531 A | 5/1980 | Aginsky |
| 4,239,113 A | 12/1980 | Gross et al. |
| 4,250,887 A | 2/1981 | Dardik et al. |
| 4,257,540 A | 3/1981 | Wegmann et al. |
| 4,268,639 A | 5/1981 | Seibel et al. |
| 4,274,163 A | 6/1981 | Malcolm et al. |
| 4,276,878 A | 7/1981 | Storz |
| 4,277,184 A | 7/1981 | Solomon |
| 4,298,144 A | 11/1981 | Pressi |
| 4,309,777 A | 1/1982 | Patil |
| 4,312,343 A | 1/1982 | LaVeen et al. |
| 4,313,434 A | 2/1982 | Segal |
| 4,326,567 A | 4/1982 | Mistarz |
| 4,338,925 A | 7/1982 | Miller |
| 4,341,691 A | 7/1982 | Anuta |
| 4,346,708 A | 8/1982 | LeVeen et al. |
| 4,349,921 A | 9/1982 | Kuntz |
| 4,359,049 A | 11/1982 | Redl et al. |
| 4,373,217 A | 2/1983 | Draenert |
| 4,380,398 A | 4/1983 | Burgess |
| 4,400,170 A | 8/1983 | McNaughton et al. |
| 4,403,989 A | 9/1983 | Christensen et al. |
| 4,404,327 A | 9/1983 | Crugnola et al. |
| 4,405,249 A | 9/1983 | Scales |
| 4,409,966 A | 10/1983 | Lambrecht et al. |
| 4,453,539 A | 6/1984 | Raftopoulos et al. |
| 4,474,572 A | 10/1984 | McNaughton et al. |
| 4,475,856 A | 10/1984 | Toomingas |
| 4,476,866 A | 10/1984 | Chin |
| 4,487,602 A | 12/1984 | Christensen et al. |
| 4,494,535 A | 1/1985 | Haig |
| 4,500,658 A | 2/1985 | Fox |
| 4,503,169 A | 3/1985 | Randklev |
| 4,522,200 A | 6/1985 | Stednitz |
| D279,499 S | 7/1985 | Case |
| 4,543,966 A | 10/1985 | Islam et al. |
| 4,546,767 A | 10/1985 | Smith |
| 4,554,914 A | 11/1985 | Kapp et al. |
| 4,558,693 A | 12/1985 | Lash et al. |
| 4,562,598 A | 1/1986 | Kranz |
| 4,576,152 A | 3/1986 | Muller et al. |
| 4,588,583 A | 5/1986 | Pietsch et al. |
| 4,593,685 A | 6/1986 | McKay et al. |
| 4,595,006 A | 6/1986 | Burke et al. |
| 4,600,118 A | 7/1986 | Martin |
| 4,605,011 A | 8/1986 | Naslund |
| 4,632,101 A | 12/1986 | Freedland |
| 4,636,217 A | 1/1987 | Ogilvie et al. |
| 4,642,099 A | 2/1987 | Phillips et al. |
| 4,650,469 A | 3/1987 | Berg et al. |
| 4,651,904 A | 3/1987 | Schuckman |
| 4,653,487 A | 3/1987 | Maale |
| 4,653,489 A | 3/1987 | Tronzo et al. |
| 4,664,298 A | 5/1987 | Shew |
| 4,664,655 A | 5/1987 | Orentreich et al. |
| 4,668,220 A | 5/1987 | Hawrylenko |
| 4,668,295 A | 5/1987 | Abipai |
| 4,670,008 A | 6/1987 | Von Albertini |
| 4,671,263 A | 6/1987 | Draenert |
| 4,676,655 A | 6/1987 | Handler |
| 4,676,781 A | 6/1987 | Phillips et al. |
| 4,686,973 A | 8/1987 | Frisch |
| 4,697,584 A | 10/1987 | Haynes |
| 4,697,929 A | 10/1987 | Muller |
| 4,704,035 A | 11/1987 | Kowalczyk |
| 4,710,179 A | 12/1987 | Haber et al. |
| 4,714,721 A | 12/1987 | Franek et al. |
| 4,717,383 A | 1/1988 | Phillips et al. |
| 4,718,910 A | 1/1988 | Draenert |
| 4,722,948 A | 2/1988 | Sanderson |
| 4,735,616 A | 4/1988 | Eibl et al. |
| 4,737,151 A | 4/1988 | Clement et al. |
| 4,747,832 A | 5/1988 | Buffet |
| 4,758,096 A | 7/1988 | Gunnarsson |
| 4,758,234 A | 7/1988 | Orentreich et al. |
| 4,759,769 A | 7/1988 | Hedman et al. |
| 4,762,515 A | 8/1988 | Grimm |
| 4,767,033 A | 8/1988 | Gemperle |
| 4,772,287 A | 9/1988 | Ray et al. |
| 4,782,118 A | 11/1988 | Fontanille et al. |
| 4,786,184 A | 11/1988 | Berezkina et al. |

(56) References Cited

U.S. PATENT DOCUMENTS

| | | |
|---|---|---|
| 4,791,150 A | 12/1988 | Braden et al. |
| 4,792,577 A | 12/1988 | Chen et al. |
| 2,067,458 A | 2/1989 | Nichols |
| 4,804,023 A | 2/1989 | Frearson |
| 4,813,870 A | 3/1989 | Pitzen |
| 4,815,454 A | 3/1989 | Dozier |
| 4,815,632 A | 3/1989 | Ball et al. |
| 4,826,053 A | 5/1989 | Keller |
| 4,830,227 A | 5/1989 | Ball et al. |
| 4,837,279 A | 6/1989 | Arroyo |
| 4,854,312 A | 8/1989 | Raftopoulos et al. |
| 4,854,482 A | 8/1989 | Bergner |
| 4,854,716 A | 8/1989 | Ziemann et al. |
| 4,863,072 A | 9/1989 | Perler |
| 4,869,906 A | 9/1989 | Dingeldein et al. |
| 4,872,936 A | 10/1989 | Engelbrecht |
| 4,892,231 A | 1/1990 | Ball |
| 4,892,550 A | 1/1990 | Huebsch |
| 4,902,649 A | 2/1990 | Kimura et al. |
| 4,904,260 A | 2/1990 | Ray et al. |
| 4,908,017 A | 3/1990 | Howson et al. |
| 4,910,259 A | 3/1990 | Kindt-Larsen et al. |
| 4,927,866 A | 5/1990 | Purrmann et al. |
| 4,932,969 A | 6/1990 | Frey et al. |
| 4,935,029 A | 6/1990 | Matsutani et al. |
| 4,944,065 A | 7/1990 | Svanberg et al. |
| 4,944,726 A | 7/1990 | Hilal et al. |
| 4,946,077 A | 8/1990 | Olsen |
| 4,946,285 A | 8/1990 | Vennemeyer |
| 4,946,901 A | 8/1990 | Lechner et al. |
| 4,961,647 A | 10/1990 | Coutts et al. |
| 4,966,601 A | 10/1990 | Draenet |
| 4,968,303 A | 11/1990 | Clarke et al. |
| 4,969,888 A | 11/1990 | Scholten et al. |
| 4,973,168 A | 11/1990 | Chan |
| 4,973,301 A | 11/1990 | Nissenkorn |
| 4,973,334 A | 11/1990 | Ziemann |
| 4,978,336 A | 12/1990 | Capozzi et al. |
| 4,983,164 A | 1/1991 | Hook et al. |
| 4,994,065 A | 2/1991 | Gibbs et al. |
| 4,995,868 A | 2/1991 | Brazier |
| 5,004,501 A | 4/1991 | Faccioli et al. |
| 5,006,112 A | 4/1991 | Metzner |
| 5,012,066 A | 4/1991 | Matsutani et al. |
| 5,015,233 A | 5/1991 | McGough et al. |
| 5,018,919 A | 5/1991 | Stephan |
| 5,022,563 A | 6/1991 | Marchito et al. |
| 5,024,232 A | 6/1991 | Smid et al. |
| 5,028,141 A | 7/1991 | Stiegelmann |
| 5,037,473 A | 8/1991 | Antonucci et al. |
| 5,049,157 A | 9/1991 | Mittelmeier et al. |
| 5,051,482 A | 9/1991 | Tepic |
| 5,059,193 A | 10/1991 | Kuslich |
| 5,059,199 A | 10/1991 | Okada et al. |
| 5,061,128 A | 10/1991 | Jahr et al. |
| 5,071,040 A | 12/1991 | Laptewicz, Jr. |
| 5,074,871 A | 12/1991 | Groshong |
| 5,078,919 A | 1/1992 | Ashley et al. |
| 5,092,888 A | 3/1992 | Iwamoto et al. |
| 5,102,413 A | 4/1992 | Poddar |
| 5,108,403 A | 4/1992 | Stern |
| 5,108,404 A | 4/1992 | Scholten et al. |
| 5,112,333 A | 5/1992 | Fixel |
| 5,114,240 A | 5/1992 | Kindt-Larsen et al. |
| 5,116,335 A | 5/1992 | Hannon |
| 5,122,400 A | 6/1992 | Stewart |
| 5,123,926 A | 6/1992 | Pisharodi |
| 5,125,971 A | 6/1992 | Nonami et al. |
| 5,131,382 A | 7/1992 | Meyer |
| 5,141,496 A | 8/1992 | Dalto et al. |
| 5,145,250 A | 9/1992 | Planck et al. |
| 5,147,903 A | 9/1992 | Podszun et al. |
| 5,171,248 A | 12/1992 | Ellis |
| 5,171,278 A | 12/1992 | Pisharodi |
| 5,181,918 A | 1/1993 | Brandhorst et al. |
| 5,188,259 A | 2/1993 | Petit |
| 5,190,191 A | 3/1993 | Reyman |
| 5,192,327 A | 3/1993 | Brantigan |
| 5,193,907 A | 3/1993 | Faccioli |
| 5,209,753 A | 5/1993 | Biedermann et al. |
| 5,217,147 A | 6/1993 | Kaufman |
| 5,219,897 A | 6/1993 | Murray |
| 5,236,445 A | 8/1993 | Hayhurst et al. |
| 5,242,983 A | 9/1993 | Kennedy et al. |
| 5,252,301 A | 10/1993 | Nilson et al. |
| 5,254,092 A | 10/1993 | Polyak |
| 5,258,420 A | 11/1993 | Posey-Dowty et al. |
| 5,264,215 A | 11/1993 | Nakabayashi et al. |
| 5,268,001 A | 12/1993 | Nicholson et al. |
| 5,269,762 A | 12/1993 | Armbruster et al. |
| 5,275,214 A | 1/1994 | Rehberger |
| 5,276,070 A | 1/1994 | Arroyo |
| 5,277,339 A | 1/1994 | Shew et al. |
| 5,279,555 A | 1/1994 | Lifshey |
| 5,290,260 A | 3/1994 | Stines |
| 5,295,980 A | 3/1994 | Ersek |
| 5,302,020 A | 4/1994 | Kruse |
| 5,303,718 A | 4/1994 | Krajicek |
| 5,304,147 A | 4/1994 | Johnson et al. |
| 5,318,532 A | 6/1994 | Frassica |
| 5,328,262 A | 7/1994 | Lidgren et al. |
| 5,328,362 A | 7/1994 | Watson et al. |
| 5,331,972 A | 7/1994 | Wadhwani et al. |
| 5,333,951 A | 8/1994 | Wakoh |
| 5,334,184 A | 8/1994 | Bimman |
| 5,334,626 A | 8/1994 | Lin |
| 5,336,699 A | 8/1994 | Cooke et al. |
| 5,336,700 A | 8/1994 | Murray |
| 5,344,232 A | 9/1994 | Nelson et al. |
| 5,348,391 A | 9/1994 | Murray |
| 5,348,548 A | 9/1994 | Meyer et al. |
| 5,350,372 A | 9/1994 | Ikeda et al. |
| 5,354,287 A | 10/1994 | Wacks |
| 5,356,382 A | 10/1994 | Picha et al. |
| 5,368,046 A | 11/1994 | Scarfone et al. |
| 5,368,386 A | 11/1994 | Murray |
| 5,370,221 A | 12/1994 | Magnusson et al. |
| 5,372,583 A | 12/1994 | Roberts et al. |
| 5,374,427 A | 12/1994 | Stille et al. |
| 5,376,123 A | 12/1994 | Klaue et al. |
| 5,380,772 A | 1/1995 | Hasegawa et al. |
| 5,385,081 A | 1/1995 | Sneddon |
| 5,385,566 A | 1/1995 | Ullmaerk |
| 5,387,191 A | 2/1995 | Hemstreet et al. |
| 5,390,683 A | 2/1995 | Pisharodi |
| 5,395,167 A | 3/1995 | Murray |
| 5,395,326 A | 3/1995 | Haber et al. |
| 5,398,483 A | 3/1995 | Smith et al. |
| 5,401,806 A | 3/1995 | Braden et al. |
| 5,407,266 A | 4/1995 | Dotsch et al. |
| 5,411,180 A | 5/1995 | Dumelle |
| 5,415,474 A | 5/1995 | Nelson et al. |
| 5,423,824 A | 6/1995 | Akerfeldt et al. |
| 5,423,850 A | 6/1995 | Berger |
| 5,431,654 A | 7/1995 | Nic |
| 5,435,645 A | 7/1995 | Faccioli |
| 5,441,502 A | 8/1995 | Bartlett |
| 5,443,182 A | 8/1995 | Tanaka et al. |
| 5,445,639 A | 8/1995 | Kuslich et al. |
| 5,450,924 A | 9/1995 | Tseng |
| 5,454,365 A | 10/1995 | Bonutti |
| 5,456,267 A | 10/1995 | Stark |
| 5,468,245 A | 11/1995 | Vargas, III |
| 5,480,400 A | 1/1996 | Berger |
| 5,480,403 A | 1/1996 | Lee |
| 5,482,187 A | 1/1996 | Poulsen et al. |
| 5,492,247 A | 2/1996 | Shu et al. |
| 5,494,349 A | 2/1996 | Seddon |
| 5,501,374 A | 3/1996 | Laufer et al. |
| 5,501,520 A | 3/1996 | Lidgren et al. |
| 5,501,695 A | 3/1996 | Anspach, Jr. et al. |
| 5,512,610 A | 4/1996 | Lin |
| 5,514,135 A | 5/1996 | Earle |
| 5,514,137 A | 5/1996 | Coutts |

(56) References Cited

U.S. PATENT DOCUMENTS

| | | |
|---|---|---|
| 5,518,498 A | 5/1996 | Lindenberg et al. |
| 5,520,690 A | 5/1996 | Errico et al. |
| 5,522,816 A | 6/1996 | Dinello et al. |
| 5,522,899 A | 6/1996 | Michelson |
| 5,526,853 A | 6/1996 | McPhee et al. |
| 5,531,519 A | 7/1996 | Earle |
| 5,531,683 A | 7/1996 | Kriesel et al. |
| 5,534,028 A | 7/1996 | Bao et al. |
| 5,536,262 A | 7/1996 | Velasquez |
| 5,545,460 A | 8/1996 | Tanaka et al. |
| 5,548,001 A | 8/1996 | Podszun et al. |
| 5,549,380 A | 8/1996 | Lidgren et al. |
| 5,549,381 A | 8/1996 | Hays et al. |
| 5,549,679 A | 8/1996 | Kuslich |
| 5,551,778 A | 9/1996 | Hauke et al. |
| 5,554,101 A | 9/1996 | Matula et al. |
| 5,556,201 A | 9/1996 | Veltrop et al. |
| 5,558,136 A | 9/1996 | Orrico |
| 5,558,639 A | 9/1996 | Gangemi et al. |
| 5,571,189 A | 11/1996 | Kuslich et al. |
| 5,573,265 A | 11/1996 | Pradel |
| 5,578,035 A | 11/1996 | Lin |
| 5,586,821 A | 12/1996 | Bonitati et al. |
| 5,588,745 A | 12/1996 | Tanaka et al. |
| 5,591,197 A | 1/1997 | Orth et al. |
| 5,601,557 A | 2/1997 | Hayhurst |
| 5,603,701 A | 2/1997 | Fisher |
| 5,609,637 A | 3/1997 | Biedermann et al. |
| 5,624,184 A | 4/1997 | Chan |
| 5,630,806 A | 5/1997 | Inagaki et al. |
| 5,634,880 A | 6/1997 | Feldman et al. |
| 5,637,097 A | 6/1997 | Yoon |
| 5,638,997 A | 6/1997 | Hawkins et al. |
| 5,641,010 A | 6/1997 | Maier |
| 5,645,598 A | 7/1997 | Brosnahan, III |
| 5,647,856 A | 7/1997 | Eykmann |
| 5,653,686 A | 8/1997 | Coulter et al. |
| 5,658,310 A | 8/1997 | Berger |
| 5,660,186 A | 8/1997 | Bachir |
| 5,665,067 A | 9/1997 | Linder et al. |
| 5,681,317 A | 10/1997 | Caldarise |
| 5,683,451 A | 11/1997 | Lenker et al. |
| 5,685,826 A | 11/1997 | Bonutti |
| 5,690,606 A | 11/1997 | Slotman |
| 5,693,100 A | 12/1997 | Pisharodi |
| 5,697,977 A | 12/1997 | Pisharodi |
| 5,698,611 A | 12/1997 | Okada et al. |
| 5,702,448 A | 12/1997 | Buechel et al. |
| 5,704,895 A | 1/1998 | Scott et al. |
| 5,707,390 A | 1/1998 | Bonutti |
| 5,718,707 A | 2/1998 | Mikhail |
| 5,720,753 A | 2/1998 | Sander et al. |
| 5,725,341 A | 3/1998 | Hofmeister |
| 5,725,529 A | 3/1998 | Nicholson et al. |
| 5,747,553 A | 5/1998 | Guzauskas |
| 5,752,935 A | 5/1998 | Robinson et al. |
| 5,752,969 A | 5/1998 | Cunci et al. |
| 5,752,974 A | 5/1998 | Rhee |
| 5,755,732 A | 5/1998 | Green et al. |
| 5,759,186 A | 6/1998 | Bachmann et al. |
| 5,763,092 A | 6/1998 | Lee et al. |
| 5,779,356 A | 7/1998 | Chan |
| 5,782,713 A | 7/1998 | Yang |
| 5,782,747 A | 7/1998 | Zimmon |
| 5,782,830 A | 7/1998 | Farris |
| 5,782,838 A | 7/1998 | Beyar et al. |
| 5,785,647 A | 7/1998 | Tompkins et al. |
| 5,785,682 A | 7/1998 | Grabenkort |
| 5,792,044 A | 8/1998 | Foley |
| 5,795,922 A | 8/1998 | Demian et al. |
| 5,797,678 A | 8/1998 | Murray |
| 5,800,169 A | 9/1998 | Muhlbauer |
| 5,800,409 A | 9/1998 | Bruce |
| 5,800,549 A | 9/1998 | Bao et al. |
| 5,800,550 A | 9/1998 | Sertich |
| 5,820,321 A | 10/1998 | Gruber |
| 5,824,087 A | 10/1998 | Aspden et al. |
| 5,826,713 A | 10/1998 | Sunago et al. |
| 5,826,753 A | 10/1998 | Fehlig et al. |
| 5,827,217 A | 10/1998 | Silver et al. |
| 5,827,289 A | 10/1998 | Reiley et al. |
| 5,829,875 A | 11/1998 | Hagel et al. |
| 5,830,194 A | 11/1998 | Anwar et al. |
| 5,836,306 A | 11/1998 | Duane et al. |
| 5,839,621 A | 11/1998 | Tada |
| 5,842,785 A | 12/1998 | Brown et al. |
| 5,865,802 A | 2/1999 | Yoon et al. |
| 5,876,116 A | 3/1999 | Barker et al. |
| 5,876,457 A | 3/1999 | Picha et al. |
| 5,882,340 A | 3/1999 | Yoon |
| 5,884,818 A | 3/1999 | Campbell |
| 5,893,488 A | 4/1999 | Hoag et al. |
| 5,893,850 A | 4/1999 | Cachia |
| 5,902,839 A | 5/1999 | Lautenschlager et al. |
| 5,911,721 A | 6/1999 | Nicholson et al. |
| 5,918,702 A | 7/1999 | Cheng et al. |
| 5,918,770 A | 7/1999 | Camm et al. |
| 5,925,051 A | 7/1999 | Mikhail |
| 5,928,239 A | 7/1999 | Mirza |
| 5,931,347 A | 8/1999 | Haubrich |
| 5,941,851 A | 8/1999 | Coffey et al. |
| 5,954,671 A | 9/1999 | O'Neill |
| 5,954,728 A | 9/1999 | Heller et al. |
| 5,961,211 A | 10/1999 | Barker et al. |
| 5,968,008 A | 10/1999 | Grams |
| 5,968,044 A | 10/1999 | Nicholson et al. |
| 5,968,999 A | 10/1999 | Ramp et al. |
| 5,972,015 A | 10/1999 | Scribner et al. |
| 5,980,527 A | 11/1999 | Cohen et al. |
| 5,993,535 A | 11/1999 | Sawamura et al. |
| 5,997,544 A | 12/1999 | Nies et al. |
| 6,004,325 A | 12/1999 | Vargas, III |
| 6,007,496 A | 12/1999 | Brannon |
| 6,017,349 A | 1/2000 | Heller et al. |
| 6,019,765 A | 2/2000 | Thornhill et al. |
| 6,019,776 A | 2/2000 | Preissman et al. |
| 6,019,789 A | 2/2000 | Dinh et al. |
| 6,020,396 A | 2/2000 | Jacobs |
| 6,022,339 A | 2/2000 | Fowles et al. |
| 6,033,105 A | 3/2000 | Barker et al. |
| 6,033,411 A | 3/2000 | Preissman |
| 6,039,761 A | 3/2000 | Li et al. |
| 6,040,408 A | 3/2000 | Koole |
| 6,041,977 A | 3/2000 | Lisi |
| 6,042,262 A | 3/2000 | Hajianpour |
| 6,045,555 A | 4/2000 | Smith et al. |
| 6,048,346 A | 4/2000 | Reiley |
| 6,049,026 A | 4/2000 | Muschler |
| 6,075,067 A | 6/2000 | Lidgren |
| 6,080,579 A | 6/2000 | Hanley, Jr. |
| 6,080,801 A | 6/2000 | Draenert et al. |
| 6,080,811 A | 6/2000 | Schehlmann et al. |
| 6,083,229 A | 7/2000 | Constantz et al. |
| 6,086,594 A | 7/2000 | Brown |
| 6,103,779 A | 8/2000 | Guzauskas |
| 6,116,773 A | 9/2000 | Murray |
| 6,120,174 A | 9/2000 | Hoag et al. |
| 6,124,373 A | 9/2000 | Peter et al. |
| 6,126,689 A | 10/2000 | Brett |
| 6,127,597 A | 10/2000 | Beyar et al. |
| 6,129,763 A | 10/2000 | Chauvin et al. |
| 6,132,396 A | 10/2000 | Antanavich et al. |
| 6,136,038 A | 10/2000 | Raab |
| 6,139,509 A | 10/2000 | Yuan et al. |
| 6,142,998 A | 11/2000 | Smith et al. |
| 6,146,401 A | 11/2000 | Yoon et al. |
| 6,149,651 A | 11/2000 | Drewry et al. |
| 6,149,655 A | 11/2000 | Constantz et al. |
| 6,149,664 A | 11/2000 | Kurz |
| 6,160,033 A | 12/2000 | Nies |
| 6,161,955 A | 12/2000 | Rademaker |
| 6,168,597 B1 | 1/2001 | Biedermann et al. |
| 6,174,935 B1 | 1/2001 | Matsunae et al. |
| 6,176,607 B1 | 1/2001 | Hajianpour |

(56) References Cited

U.S. PATENT DOCUMENTS

| | | |
|---|---|---|
| 6,183,441 B1 | 2/2001 | Kriesel et al. |
| 6,183,516 B1 | 2/2001 | Burkinshaw et al. |
| 6,187,015 B1 | 2/2001 | Brenneman |
| 6,190,381 B1 | 2/2001 | Olsen et al. |
| 6,206,058 B1 | 3/2001 | Nagel et al. |
| 6,210,031 B1 | 4/2001 | Murray |
| 6,214,012 B1 | 4/2001 | Karpman et al. |
| 6,214,016 B1 | 4/2001 | Williams et al. |
| 6,214,037 B1 | 4/2001 | Mitchell et al. |
| 6,217,566 B1 | 4/2001 | Ju et al. |
| 6,217,581 B1 | 4/2001 | Tolson |
| 6,217,608 B1 | 4/2001 | Penn et al. |
| 6,221,029 B1 | 4/2001 | Mathis et al. |
| 6,224,604 B1 | 5/2001 | Suddaby |
| 6,228,049 B1 | 5/2001 | Schroeder et al. |
| 6,228,068 B1 | 5/2001 | Yoon |
| 6,228,082 B1 | 5/2001 | Baker et al. |
| 6,231,615 B1 | 5/2001 | Preissman |
| 6,235,043 B1 | 5/2001 | Reiley et al. |
| 6,238,399 B1 | 5/2001 | Heller et al. |
| 6,241,734 B1 | 6/2001 | Scribner et al. |
| 6,245,101 B1 | 6/2001 | Drasler et al. |
| 6,248,110 B1 | 6/2001 | Reiley et al. |
| 6,254,268 B1 | 7/2001 | Long |
| 6,261,289 B1 | 7/2001 | Levy |
| 6,264,618 B1 | 7/2001 | Landi et al. |
| 6,264,659 B1 | 7/2001 | Ross et al. |
| 6,264,660 B1 | 7/2001 | Schmidt et al. |
| 6,273,916 B1 | 8/2001 | Murphy |
| 6,281,271 B1 | 8/2001 | Rumphorst et al. |
| 6,309,395 B1 | 10/2001 | Smith et al. |
| 6,309,420 B1 | 10/2001 | Preissman |
| 6,312,149 B1 | 11/2001 | Sjovall et al. |
| 6,325,812 B1 | 12/2001 | Dubrul et al. |
| 6,348,055 B1 | 2/2002 | Preissman |
| 6,348,518 B1 | 2/2002 | Montgomery |
| 6,350,271 B1 | 2/2002 | Kurz et al. |
| 6,361,539 B1 | 3/2002 | Heller et al. |
| 6,364,865 B1 | 4/2002 | Lavi et al. |
| 6,367,962 B1 | 4/2002 | Mizutani et al. |
| 6,375,659 B1 | 4/2002 | Erbe et al. |
| 6,375,682 B1 | 4/2002 | Fleischmann et al. |
| 6,383,188 B2 | 5/2002 | Kuslich et al. |
| 6,383,190 B1 | 5/2002 | Preissman |
| 6,395,007 B1 | 5/2002 | Bhatnagar |
| 6,402,701 B1 | 6/2002 | Kaplan et al. |
| 6,402,758 B1 | 6/2002 | Tolson |
| 6,406,175 B1 | 6/2002 | Marino |
| 6,409,972 B1 | 6/2002 | Chan |
| 6,410,612 B1 | 6/2002 | Hatanaka |
| 6,425,887 B1 | 7/2002 | McGuckin et al. |
| 6,431,743 B1 | 8/2002 | Mizutani et al. |
| 6,433,037 B1 | 8/2002 | Guzauskas |
| 6,436,143 B1 | 8/2002 | Ross et al. |
| 6,439,439 B1 | 8/2002 | Rickard |
| 6,443,334 B1 | 9/2002 | John et al. |
| 6,447,478 B1 | 9/2002 | Maynards |
| 6,450,973 B1 | 9/2002 | Murphy |
| 6,458,117 B1 | 10/2002 | Pollins, Sr. |
| 6,479,565 B1 | 11/2002 | Stanley |
| 6,488,667 B1 | 12/2002 | Murphy |
| 6,494,868 B2 | 12/2002 | Amar |
| 6,500,182 B2 | 12/2002 | Foster |
| 6,502,608 B1 | 1/2003 | Burchett et al. |
| 6,527,144 B2 | 3/2003 | Ritsche et al. |
| 6,550,957 B2 | 4/2003 | Mizutani et al. |
| 6,554,833 B2 | 4/2003 | Levy et al. |
| 6,568,439 B1 | 5/2003 | Se et al. |
| 6,572,256 B2 | 6/2003 | Seaton et al. |
| 6,575,331 B1 | 6/2003 | Peeler et al. |
| 6,575,919 B1 | 6/2003 | Reilley et al. |
| 6,582,439 B1 | 6/2003 | Sproul |
| 6,592,559 B2 | 7/2003 | Pakter et al. |
| 6,595,967 B2 | 7/2003 | Kramer |
| 6,599,293 B2 | 7/2003 | Tague et al. |
| 6,599,520 B2 | 7/2003 | Scarborough et al. |
| 6,613,018 B2 | 9/2003 | Bagga |
| 6,613,054 B2 | 9/2003 | Scribner et al. |
| 6,626,912 B2 | 9/2003 | Speitling |
| 6,641,587 B2 | 11/2003 | Scribner et al. |
| 6,645,213 B2 | 11/2003 | Sand et al. |
| 6,662,969 B2 | 12/2003 | Peeler et al. |
| 6,676,664 B1 | 1/2004 | Al-Assir |
| 6,689,823 B1 | 2/2004 | Bellare et al. |
| 6,702,455 B2 | 3/2004 | Vendrely et al. |
| 6,712,853 B2 | 3/2004 | Kuslich |
| 6,716,216 B1 | 4/2004 | Boucher et al. |
| 6,719,761 B1 | 4/2004 | Reiley et al. |
| 6,720,417 B1 | 4/2004 | Walter |
| 6,730,095 B2 | 5/2004 | Olson, Jr. et al. |
| 6,752,180 B2 | 6/2004 | Delay |
| 6,758,837 B2 | 7/2004 | Peciat et al. |
| 6,759,449 B2 | 7/2004 | Kimura et al. |
| 6,767,973 B2 | 7/2004 | Suau et al. |
| 6,770,079 B2 | 8/2004 | Bhatnagar |
| 6,779,566 B2 | 8/2004 | Engel |
| 6,780,175 B1 | 8/2004 | Sachdeva et al. |
| 6,783,515 B1 | 8/2004 | Miller et al. |
| 6,787,584 B2 | 9/2004 | Jia et al. |
| 6,796,987 B2 | 9/2004 | Tague et al. |
| 6,852,439 B2 | 2/2005 | Frank |
| 6,874,927 B2 | 4/2005 | Foster |
| 6,875,219 B2 | 4/2005 | Arramon et al. |
| 6,887,246 B2 | 5/2005 | Bhatnagar |
| 6,916,308 B2 | 7/2005 | Dixon et al. |
| 6,957,747 B2 | 10/2005 | Peeler et al. |
| 6,974,247 B2 | 12/2005 | Frei et al. |
| 6,974,416 B2 | 12/2005 | Booker et al. |
| 6,979,341 B2 | 12/2005 | Scribner et al. |
| 6,979,352 B2 | 12/2005 | Reynolds |
| 6,994,465 B2 | 2/2006 | Tague et al. |
| 6,997,930 B1 | 2/2006 | Jäggi et al. |
| 7,008,433 B2 | 3/2006 | Voellmicke et al. |
| 7,025,771 B2 | 4/2006 | Kuslich et al. |
| 7,029,163 B2 | 4/2006 | Barker et al. |
| 7,044,954 B2 | 5/2006 | Reiley |
| 7,048,743 B2 | 5/2006 | Miller |
| 7,066,942 B2 | 6/2006 | Treace |
| 7,087,040 B2 | 8/2006 | McGuckin |
| 7,091,258 B2 | 8/2006 | Neubert et al. |
| 7,097,648 B1 | 8/2006 | Globerman et al. |
| 7,112,205 B2 | 9/2006 | Carrison |
| 7,116,121 B1 | 10/2006 | Holcombe et al. |
| 7,252,671 B2 | 8/2007 | Scribner |
| 7,264,622 B2 | 9/2007 | Michelson |
| 7,270,667 B2 | 9/2007 | Faccioli |
| 7,278,778 B2 | 10/2007 | Sand |
| 7,320,540 B2 | 1/2008 | Coffeen |
| 7,326,203 B2 | 2/2008 | Papineau et al. |
| 7,456,024 B2 | 11/2008 | Dahm et al. |
| 7,470,258 B2 | 12/2008 | Barker et al. |
| 7,559,932 B2 | 7/2009 | Truckai et al. |
| 7,572,263 B2 | 8/2009 | Preismann |
| 7,604,618 B2 | 10/2009 | Dixon et al. |
| 7,666,205 B2 | 2/2010 | Weikel et al. |
| 7,678,116 B2 | 3/2010 | Truckai et al. |
| 7,717,918 B2 | 5/2010 | Truckai et al. |
| 7,722,620 B2 | 5/2010 | Truckai et al. |
| 8,038,682 B2 | 10/2011 | McGill et al. |
| 8,066,713 B2 | 11/2011 | DiMauro et al. |
| 8,070,753 B2 | 12/2011 | Truckai et al. |
| 8,333,773 B2 | 12/2012 | DiMauro et al. |
| 8,360,629 B2 | 1/2013 | Globerman et al. |
| 8,361,078 B2 | 1/2013 | Beyar et al. |
| 8,415,407 B2 | 4/2013 | Beyar et al. |
| 8,540,722 B2 | 9/2013 | Beyar et al. |
| 8,809,418 B2 | 8/2014 | Beyar et al. |
| 8,950,929 B2 | 2/2015 | Globerman et al. |
| 8,956,368 B2 | 2/2015 | Beyar et al. |
| 9,186,194 B2 | 11/2015 | Ferreyro et al. |
| 9,259,696 B2 | 2/2016 | Globerman et al. |
| 9,381,024 B2 | 7/2016 | Globerman et al. |
| 9,504,508 B2 | 11/2016 | Beyar et al. |
| 2001/0012968 A1 | 8/2001 | Preissman |

(56) References Cited

U.S. PATENT DOCUMENTS

| | | |
|---|---|---|
| 2001/0024400 A1 | 9/2001 | Van Der Wel |
| 2001/0034527 A1 | 10/2001 | Scribner et al. |
| 2002/0008122 A1 | 1/2002 | Ritsche et al. |
| 2002/0010471 A1 | 1/2002 | Wironen |
| 2002/0010472 A1 | 1/2002 | Kuslich et al. |
| 2002/0013553 A1 | 1/2002 | Pajunk |
| 2002/0049448 A1 | 4/2002 | Sand et al. |
| 2002/0049449 A1 | 4/2002 | Bhatnagar et al. |
| 2002/0058947 A1 | 5/2002 | Hochschuler et al. |
| 2002/0067658 A1 | 6/2002 | Vendrely et al. |
| 2002/0068939 A1 | 6/2002 | Levy et al. |
| 2002/0068974 A1 | 6/2002 | Kuslich et al. |
| 2002/0068975 A1 | 6/2002 | Teitelbaum et al. |
| 2002/0072768 A1 | 6/2002 | Ginn |
| 2002/0082605 A1 | 6/2002 | Reiley et al. |
| 2002/0099384 A1 | 7/2002 | Scribner et al. |
| 2002/0099385 A1 | 7/2002 | Ralph et al. |
| 2002/0118595 A1 | 8/2002 | Miller |
| 2002/0123716 A1 | 9/2002 | VanDiver et al. |
| 2002/0156483 A1 | 10/2002 | Voellicke et al. |
| 2002/0161373 A1 | 10/2002 | Osorio et al. |
| 2002/0177866 A1 | 11/2002 | Weikel et al. |
| 2002/0183851 A1 | 12/2002 | Spiegelberg et al. |
| 2002/0188300 A1 | 12/2002 | Arramon |
| 2002/0191487 A1 | 12/2002 | Sand |
| 2003/0009177 A1 | 1/2003 | Middleman et al. |
| 2003/0018339 A1 | 1/2003 | Higueras et al. |
| 2003/0031698 A1 | 2/2003 | Roeder et al. |
| 2003/0032929 A1 | 2/2003 | McGuckin |
| 2003/0036763 A1 | 2/2003 | Bhatnagar et al. |
| 2003/0040718 A1 | 2/2003 | Keahey et al. |
| 2003/0050644 A1 | 3/2003 | Boucher et al. |
| 2003/0050702 A1 | 3/2003 | Berger |
| 2003/0078589 A1 | 4/2003 | Preissman |
| 2003/0109883 A1 | 6/2003 | Matsuzaki et al. |
| 2003/0109884 A1 | 6/2003 | Tague et al. |
| 2003/0144742 A1 | 7/2003 | King et al. |
| 2003/0162864 A1 | 8/2003 | Pearson et al. |
| 2003/0174576 A1 | 9/2003 | Tague et al. |
| 2003/0181963 A1 | 9/2003 | Pellegrino et al. |
| 2003/0185093 A1 | 10/2003 | Vendrely et al. |
| 2003/0220414 A1 | 11/2003 | Axen et al. |
| 2003/0225364 A1 | 12/2003 | Kraft et al. |
| 2003/0227816 A1 | 12/2003 | Okamoto et al. |
| 2003/0231545 A1 | 12/2003 | Seaton |
| 2004/0010263 A1 | 1/2004 | Boucher et al. |
| 2004/0029996 A1 | 2/2004 | Kuhn |
| 2004/0054377 A1 | 3/2004 | Foster et al. |
| 2004/0059283 A1 | 3/2004 | Kirwan et al. |
| 2004/0066706 A1 | 4/2004 | Barker et al. |
| 2004/0068264 A1 | 4/2004 | Treace |
| 2004/0073139 A1 | 4/2004 | Hirsch et al. |
| 2004/0092946 A1 | 5/2004 | Bagga et al. |
| 2004/0098015 A1 | 5/2004 | Weikel et al. |
| 2004/0106913 A1 | 6/2004 | Eidenschink et al. |
| 2004/0122438 A1 | 6/2004 | Abrams |
| 2004/0132859 A1 | 7/2004 | Puckett, Jr et al. |
| 2004/0133124 A1 | 7/2004 | Bates et al. |
| 2004/0133211 A1 | 7/2004 | Raskin et al. |
| 2004/0138759 A1 | 7/2004 | Muller et al. |
| 2004/0157952 A1 | 8/2004 | Soffiati et al. |
| 2004/0157954 A1 | 8/2004 | Imai et al. |
| 2004/0162559 A1 | 8/2004 | Arramon et al. |
| 2004/0167532 A1 | 8/2004 | Olson et al. |
| 2004/0167562 A1 | 8/2004 | Osorio et al. |
| 2004/0167625 A1 | 8/2004 | Beyar et al. |
| 2004/0193171 A1 | 9/2004 | DiMauro et al. |
| 2004/0215202 A1 | 10/2004 | Preissman |
| 2004/0220672 A1 | 11/2004 | Shadduck |
| 2004/0226479 A1 | 11/2004 | Lyles et al. |
| 2004/0229972 A1 | 11/2004 | Klee et al. |
| 2004/0230309 A1 | 11/2004 | DiMauro et al. |
| 2004/0236313 A1 | 11/2004 | Klein |
| 2004/0249015 A1 | 12/2004 | Jia et al. |
| 2004/0249347 A1 | 12/2004 | Miller et al. |
| 2004/0260303 A1 | 12/2004 | Carrison |
| 2004/0260304 A1 | 12/2004 | Faccioli et al. |
| 2004/0267154 A1 | 12/2004 | Sutton et al. |
| 2005/0014273 A1 | 1/2005 | Dahm |
| 2005/0015148 A1 | 1/2005 | Jansen et al. |
| 2005/0025622 A1 | 2/2005 | Djeridane et al. |
| 2005/0058717 A1 | 3/2005 | Yetlinler et al. |
| 2005/0060023 A1 | 3/2005 | Mitchell et al. |
| 2005/0070912 A1 | 3/2005 | Voellmicke |
| 2005/0070914 A1 | 3/2005 | Constantz et al. |
| 2005/0070915 A1 | 3/2005 | Mazzuca |
| 2005/0083782 A1 | 4/2005 | Gronau et al. |
| 2005/0113762 A1 | 5/2005 | Kay et al. |
| 2005/0143827 A1 | 6/2005 | Globerman et al. |
| 2005/0154081 A1 | 7/2005 | Yin et al. |
| 2005/0180806 A1 | 8/2005 | Green |
| 2005/0203206 A1 | 9/2005 | Trieu |
| 2005/0209695 A1 | 9/2005 | de Vries et al. |
| 2005/0216025 A1 | 9/2005 | Chern Lin et al. |
| 2005/0256220 A1 | 11/2005 | Lavergne et al. |
| 2005/0281132 A1 | 12/2005 | Armstrong et al. |
| 2006/0035997 A1 | 2/2006 | Orlowski et al. |
| 2006/0041033 A1 | 2/2006 | Bisig et al. |
| 2006/0052794 A1 | 3/2006 | McGill |
| 2006/0074433 A1 | 4/2006 | McGill et al. |
| 2006/0079905 A1 | 4/2006 | Beyar et al. |
| 2006/0116643 A1 | 6/2006 | Dixon et al. |
| 2006/0116689 A1 | 6/2006 | Albans et al. |
| 2006/0116690 A1 | 6/2006 | Pagano |
| 2006/0122614 A1 | 6/2006 | Truckai et al. |
| 2006/0148923 A1 | 7/2006 | Ashman et al. |
| 2006/0167148 A1 | 7/2006 | Engquist et al. |
| 2006/0181959 A1 | 8/2006 | Weiss et al. |
| 2006/0235338 A1 | 10/2006 | Pacheco |
| 2006/0241644 A1 | 10/2006 | Osorio et al. |
| 2006/0264695 A1 | 11/2006 | Viole et al. |
| 2006/0264967 A1 | 11/2006 | Ferreyro et al. |
| 2006/0266372 A1 | 11/2006 | Miller et al. |
| 2006/0271061 A1 | 11/2006 | Beyar et al. |
| 2006/0276819 A1 | 12/2006 | Osorio et al. |
| 2007/0027230 A1 | 2/2007 | Beyar et al. |
| 2007/0032567 A1 | 2/2007 | Beyar et al. |
| 2007/0055266 A1 | 3/2007 | Osorio et al. |
| 2007/0055267 A1 | 3/2007 | Osorio et al. |
| 2007/0055278 A1 | 3/2007 | Osorio et al. |
| 2007/0055280 A1 | 3/2007 | Osorio et al. |
| 2007/0055284 A1 | 3/2007 | Osorio et al. |
| 2007/0055285 A1 | 3/2007 | Osorio |
| 2007/0055300 A1 | 3/2007 | Osorio et al. |
| 2007/0060941 A1 | 3/2007 | Reiley et al. |
| 2007/0118142 A1 | 5/2007 | Krueger |
| 2007/0142842 A1 | 6/2007 | Krueger |
| 2007/0197935 A1 | 8/2007 | Reiley et al. |
| 2007/0198013 A1 | 8/2007 | Foley et al. |
| 2007/0198023 A1 | 8/2007 | Sand et al. |
| 2007/0198024 A1 | 8/2007 | Plishka et al. |
| 2007/0255282 A1 | 11/2007 | Simonton et al. |
| 2007/0282443 A1 | 12/2007 | Globerman et al. |
| 2008/0039856 A1 | 2/2008 | DiMauro |
| 2008/0044374 A1 | 2/2008 | Lavergne et al. |
| 2008/0058827 A1 | 3/2008 | Osorio et al. |
| 2008/0065087 A1 | 3/2008 | Osorio et al. |
| 2008/0065089 A1 | 3/2008 | Osorio et al. |
| 2008/0065137 A1 | 3/2008 | Boucher et al. |
| 2008/0065142 A1 | 3/2008 | Reiley et al. |
| 2008/0065190 A1 | 3/2008 | Osorio et al. |
| 2008/0071283 A1 | 3/2008 | Osorio et al. |
| 2008/0086133 A1 | 4/2008 | Kuslich et al. |
| 2008/0132935 A1 | 6/2008 | Osorio et al. |
| 2008/0140079 A1 | 6/2008 | Osorio et al. |
| 2008/0140084 A1 | 6/2008 | Osorio et al. |
| 2008/0200915 A1 | 8/2008 | Globerman et al. |
| 2008/0212405 A1 | 9/2008 | Globerman et al. |
| 2008/0228192 A1 | 9/2008 | Beyar et al. |
| 2009/0264892 A1 | 10/2009 | Beyar et al. |
| 2009/0264942 A1 | 10/2009 | Beyar et al. |
| 2009/0270872 A1 | 10/2009 | DiMauro |
| 2010/0065154 A1 | 3/2010 | Globerman |
| 2010/0069786 A1 | 3/2010 | Globerman |

(56) References Cited

U.S. PATENT DOCUMENTS

| | | | |
|---|---|---|---|
| 2010/0152855 | A1 | 6/2010 | Kuslich et al. |
| 2010/0168271 | A1 | 7/2010 | Beyar |
| 2010/0268231 | A1 | 10/2010 | Kuslich et al. |
| 2012/0307586 | A1 | 12/2012 | Globerman et al. |
| 2013/0123791 | A1 | 5/2013 | Beyar et al. |
| 2013/0261217 | A1 | 10/2013 | Beyar et al. |
| 2013/0345708 | A1 | 12/2013 | Beyar et al. |
| 2014/0088605 | A1 | 3/2014 | Ferreyro et al. |
| 2014/0148866 | A1 | 5/2014 | Globerman et al. |
| 2015/0122691 | A1 | 5/2015 | Globerman et al. |
| 2015/0127058 | A1 | 5/2015 | Beyar et al. |
| 2015/0148777 | A1 | 5/2015 | Ferreyro et al. |
| 2016/0051302 | A1 | 2/2016 | Ferreyro et al. |

FOREIGN PATENT DOCUMENTS

| | | |
|---|---|---|
| CN | 1138001 A | 12/1996 |
| CN | 1310026 A | 8/2001 |
| DE | 136018 C | 11/1902 |
| DE | 226956 | 3/1909 |
| DE | 868497 C | 2/1953 |
| DE | 1283448 | 11/1968 |
| DE | 1810799 | 6/1970 |
| DE | 2821785 | 11/1979 |
| DE | 3003947 | 8/1980 |
| DE | 2947875 | 4/1981 |
| DE | 3443167 | 6/1986 |
| DE | 8716073 | 3/1988 |
| DE | 3817101 | 11/1989 |
| DE | 3730298 | 2/1990 |
| DE | 4104092 | 8/1991 |
| DE | 293485 | 9/1991 |
| DE | 4016135 | 3/1992 |
| DE | 4315757 | 11/1994 |
| DE | 19612276 | 10/1997 |
| DE | 10258140 | 7/2004 |
| EP | 20207 | 6/1908 |
| EP | 486638 | 6/1938 |
| EP | 0044877 | 2/1982 |
| EP | 0190504 | 3/1986 |
| EP | 0177781 | 4/1986 |
| EP | 0 235 905 A1 | 9/1987 |
| EP | 0235905 | 9/1987 |
| EP | 0301759 | 7/1988 |
| EP | 0242672 | 9/1989 |
| EP | 0425200 | 10/1990 |
| EP | 0423916 | 4/1991 |
| EP | 0475077 | 3/1992 |
| EP | 0511868 | 4/1992 |
| EP | 0493789 | 7/1992 |
| EP | 0581387 | 2/1994 |
| EP | 0614653 | 9/1994 |
| EP | 0669100 | 8/1995 |
| EP | 0748615 | 12/1996 |
| EP | 0763348 | 3/1997 |
| EP | 1 074 231 A1 | 2/2001 |
| EP | 1074231 | 2/2001 |
| EP | 1095667 | 5/2001 |
| EP | 1103237 | 5/2001 |
| EP | 1104260 | 6/2001 |
| EP | 1 247 454 A1 | 10/2002 |
| EP | 1464292 | 10/2004 |
| EP | 1 517 655 A1 | 3/2005 |
| EP | 1148850 | 4/2005 |
| EP | 1552797 | 7/2005 |
| EP | 1570873 | 9/2005 |
| EP | 1 596 896 A2 | 11/2005 |
| EP | 1598 015 | 11/2005 |
| EP | 1148851 | 5/2006 |
| EP | 1829518 | 9/2007 |
| EP | 1 886 648 A1 | 2/2008 |
| EP | 1886647 | 2/2008 |
| FR | 1548575 | 10/1968 |
| FR | 2606282 | 5/1988 |
| FR | 2629337 | 10/1989 |
| FR | 2638972 | 5/1990 |
| FR | 2674119 | 9/1992 |
| FR | 2690332 | 10/1993 |
| FR | 2712486 | 5/1995 |
| FR | 2722679 | 1/1996 |
| GB | 8331 | 0/1904 |
| GB | 179502045 | 0/1795 |
| GB | 190720207 A | 6/1908 |
| GB | 408668 | 4/1934 |
| GB | 486638 A | 6/1938 |
| GB | 2114005 | 8/1983 |
| GB | 2156824 | 10/1985 |
| GB | 2197691 | 5/1988 |
| GB | 2268068 | 1/1994 |
| GB | 2276560 | 10/1994 |
| GB | 2411849 | 9/2005 |
| GB | 2413280 | 10/2005 |
| GB | 2469749 | 10/2010 |
| JP | 51-134465 A | 11/1976 |
| JP | 54-009110 | 1/1979 |
| JP | 55-009242 U | 1/1980 |
| JP | 55-109440 | 8/1980 |
| JP | 62-068893 | 3/1987 |
| JP | 63-194722 A | 8/1988 |
| JP | 02-122017 | 5/1990 |
| JP | 02-166235 | 6/1990 |
| JP | 02-125730 U | 10/1990 |
| JP | 4 329956 | 11/1992 |
| JP | 07-000410 | 1/1995 |
| JP | 8322848 | 12/1996 |
| JP | 10146559 | 6/1998 |
| JP | 10-511569 | 10/1998 |
| JP | 2001-514922 A | 9/2001 |
| JP | 2004-16707 | 1/2004 |
| JP | 2005-500103 A | 1/2005 |
| JP | 2008-55367 | 3/2008 |
| RO | 116784 | 6/2001 |
| RU | 1011119 | 4/1983 |
| RU | 1049050 | 10/1983 |
| SU | 662082 | 5/1979 |
| WO | 88/10129 A1 | 12/1988 |
| WO | WO 90/00037 | 1/1990 |
| WO | WO 92/14423 | 9/1992 |
| WO | WO 94/12112 | 6/1994 |
| WO | WO 95/13862 | 5/1995 |
| WO | WO 96/11643 | 4/1996 |
| WO | WO 96/19940 | 7/1996 |
| WO | WO 96/32899 | 10/1996 |
| WO | WO 96/37170 | 11/1996 |
| WO | WO 97/18769 | 5/1997 |
| WO | WO 97/28835 | 8/1997 |
| WO | WO 98/28035 | 7/1998 |
| WO | WO 98/38918 | 9/1998 |
| WO | WO 99/18866 | 4/1999 |
| WO | WO 99/18894 | 4/1999 |
| WO | WO 99/29253 | 6/1999 |
| WO | WO 99/37212 | 7/1999 |
| WO | WO 99/39661 | 8/1999 |
| WO | WO 99/49819 | 10/1999 |
| WO | WO 99/52446 | 10/1999 |
| WO | WO 00/06216 | 2/2000 |
| WO | WO 00/44319 | 8/2000 |
| WO | WO 00/44321 | 8/2000 |
| WO | WO 00/44946 | 8/2000 |
| WO | WO 00/54705 | 9/2000 |
| WO | WO 00/56254 | 9/2000 |
| WO | WO 01/08571 | 2/2001 |
| WO | WO 01/13822 | 3/2001 |
| WO | WO 01/54598 | 8/2001 |
| WO | WO 01/60270 | 8/2001 |
| WO | WO 01/76514 | 10/2001 |
| WO | WO 02/00143 | 1/2002 |
| WO | WO 02/02033 | 1/2002 |
| WO | WO 02/19933 | 3/2002 |
| WO | 02/064195 A2 | 8/2002 |
| WO | WO 02/064062 | 8/2002 |
| WO | WO 02/064194 | 8/2002 |
| WO | WO 02/072156 | 9/2002 |
| WO | WO 02/096474 | 12/2002 |

(56) References Cited

FOREIGN PATENT DOCUMENTS

| | | |
|---|---|---|
| WO | WO 03/007854 | 1/2003 |
| WO | WO 03/015845 | 2/2003 |
| WO | WO 03/022165 | 3/2003 |
| WO | WO 03/061495 | 7/2003 |
| WO | WO 03/078041 | 9/2003 |
| WO | WO 03/101596 | 12/2003 |
| WO | WO 2004/002375 | 1/2004 |
| WO | WO 2004/001980 | 3/2004 |
| WO | WO 2004/019810 | 3/2004 |
| WO | WO 2004/071543 | 8/2004 |
| WO | 2004/080357 | 9/2004 |
| WO | WO 2004/075965 | 9/2004 |
| WO | WO 2004/080357 | 9/2004 |
| WO | WO 2004/110292 | 12/2004 |
| WO | WO 2004/110300 | 12/2004 |
| WO | WO 2005/000138 | 1/2005 |
| WO | 2005/017000 A1 | 2/2005 |
| WO | WO 2005/032326 | 4/2005 |
| WO | WO 2005/048867 | 6/2005 |
| WO | WO 2005/051212 | 6/2005 |
| WO | WO 2005/110259 | 11/2005 |
| WO | WO 2006/011152 | 2/2006 |
| WO | WO 2006/039159 | 4/2006 |
| WO | 2006/062939 A2 | 6/2006 |
| WO | WO 2006/090379 | 8/2006 |
| WO | WO 2006090379 A2 * | 8/2006 |
| WO | WO 2007/015202 | 2/2007 |
| WO | WO 2007/036815 | 4/2007 |
| WO | WO 2007/148336 | 12/2007 |
| WO | WO 2008/004229 | 1/2008 |
| WO | WO 2008/032322 | 3/2008 |
| WO | WO 2008/047371 | 4/2008 |

OTHER PUBLICATIONS

International Search Report, for PCT/IL07/00808, issued Aug. 22, 2008.
Marks, Standard handbook for mechanical engineers, section 5 (Tenth ed. 1996).
Supp. EP Search Report, from EP 07766838.2, dated May 18, 2011.
Al-Assir et al., "Percutaneous Vertebroplasty: A Special Syringe for Cement Injection," AJNR Am. J. Neuroradiol. 21:159-61 (2000).
Baroud et al., "Injection Biomechanics of Bone Cements Used in Vertebroplasty," Biomed. Mat. & Eng. 00:1-18 (2004).
Cole et al., "AIM Titanium Humeral Nail System," Surgical Technique. DePuy Orthopaedics 17P (2000).
Farrar, D.F. et al., "Rheological Properties of PMMA Bone Cements During Curing," Biomaterials 22:3005-13 (2001).
Heini et al., "The Use of a Side-Opening Injection Cannula in Vertebroplasty," Spine 27(1):105-09 (2002).
Hernandez et al., "Influence of Powder Particle Size Distribution on Complex Viscosity and Other Properties of Acrylic Bone Cement for Vertebroplasty and Kyphoplasty," J. Biomed. Mat. Res. 77B:98-103 (2006).
International Search Report, for PCT/MX03/00027, filed Mar. 14, 2003.
Ishikawa et al., "Effects of Neutral Sodium Hydrogen Phosphate on Setting Reaction and Mechanical Strength of Hydroxyapatite Putty," J. Biomed. Mat. Res. 44:322-29, (1999).
Ishikawa et al., "Non-Decay Type Fast-Setting Calcium Phosphate Cement: Hydroxyapatite Putty Containing an Increased Amount of Sodium Alginate," J. Biomed. Mat. Res. 36:393-99 (1997).
Kallmes et al., "Radiation Dose to the Operator During Vertebroplasty: Prospective Comparison of the Use of 1-cc Syringes Versus an Injection Device," AJNR Am. J. Neuroradiol. 24:1257-60 (2003).
Krause et al., "The Viscosity of Acrylic Bone Cements," J. Biomed. Mat. Res. 16:219-43 (1982).
Lewis, "Properties of Ascrylic Bone Cement: State of the Art Review," J. Biomed. Mat. Res. Appl. Biomaterials 38(2):155-82 (p. 158 s.Viscosity) (1997).
Lewis, "Toward Standardization of Methods of Determination of Fracture Properties of Acrylic Bone Cement and Statistical Analysis of Test Results," J. Biomed. Research: Appl. Biomaterials 53(6):748-68 (2000).
Mousa, W.F. et al., "Biological and Mechanical Properties of PMMA-Based Bioactive Bone Cements," Biomaterials 21:2137-46 (2000).
Nussbaum et al., "The Chemistry of Acrylic Bone Cements and Implications for Clinical Use in Image-Guided Therapy," J. Vasc. Interv. Radiol. 15:121-26 (2004).
Serbetci, K. et al., "Thermal and Mechanical Properties of Hydroxyapatite Impregnated Acrylic Bone Cements," Polymer Testing 23:145-55 (2004).
Steen, "Laser Surface Treatment," Laser Mat. Processing, Springer 2d ed. ch. 6:218-71 (2003).
Supp EP Search Report, from EP Appl No. 05763930.4, dated Sep. 11, 2008.
Supp EP Search Report, from EP Appl No. 06711221.9, dated Sep. 15, 2008.
Varela et al., "Closed Intramedullary Pinning of Metacarpal and Phalanx Fractures," Orthopaedics 13(2):213-15 (1990).
Weissman et al., "Trochanteric Fractures of the Femur Treatment with a Strong Nail and early Weight-Bearing," Clin. Ortho. & Related Res. 67:143-50 (1969).
Bohner, M. et al., "Theoretical and Experimental Model to Describe the Injection of a Polymethacrylate Cement into a Porous Structure," Biomaterials 24(16):2721-30 (2003).
Breusch, S. et al., "Knochenzemente auf Basis von Polymethylmethacrylat," Orthopade 32:41-50 (2003).
Carrodegus et al., "Injectable Acrylic Bone Cements for Vertebroplasty with Improved Properties," J. Biomed. Materials Res. 68(1):94-104 (Jan. 2004).
Gheduzzi, S. et al., "Mechanical Characterisation of Three Percutaneous Vertebroplasty Biomaterials," J. Mater Sci Mater Med 17(5):421-26 (2006).
Giannitsios, D. et al., "High Cement Viscosity Reduces Leakage Risk in Vertebroplasty," European Cells & Mat. 10 supp. 3:54 (2005).
Hasenwinkel, J. et al., "A Novel High-Viscosity, Two-Solution Acrylic Bone Cement: Effect of Chemical Composition on Properties," J. Biomed. Materials Research 47(1):36-45 (1999).
Hasenwinkel, J. et al., "Effect of Initiation Chemistry on the Fracture Toughness, Fatigue Strength, and Residual Monomer Content of a Novel High-Viscosity, Two-Solution Acrylic Bone Cement," J. Biomed. Materials Res. 59(3):411-21 (2001).
Lewis, G. et al., "Rheological Properties of Acrylic Bone Cement During Curing and the Role of the Size of the Powder Particles," J. Biomed. Mat. Res. Appl. Biomat. 63(2):191-99 (2002).
Pascual, B. et al., "New Aspects of the Effect of Size and Size Distribution on the Setting Parameters and Mechanical Properties of Acrylic Bone Cements," Biomaterials 17(5):509-16 (1996).
Robinson, R. et al., "Mechanical Properties of Poly(methyl methacrylate) Bone Cement," J. Biomed. Materials Res. 15(2):203-08 (2004).
Saha, S. et a., "Mechanical Properties of Bone Cement: A Review," J. Biomed. Materilas Res. 18(4):435-62 (1984).
Andersen, M. et al., "Vertebroplastik, ny behandling af osteoporotiske columnafrakturer?", Ugeskr Laefer 166/6:463-66 (Feb. 2, 2004).
Zapalowicz, K. et al., "Percutaneous Vertebroplasty with Bone Cement in the Treatment of Osteoporotic Vertebral Compression Fractures," Ortopedia Traumatologia Rehabilitacja NR Jan. 2003.
Chinese Office Action, from CN Appl No. 200680013255.5, mailed Jan. 23, 2009.
European Communication, from EP Appl No. 06711221.9, mailed Nov. 24, 2008.
European Search Report, from EP05763930.4; mailed Sep. 11, 2008.
International Search Report, from PCT/IL06/00239, mailed Jan. 26, 2007.
International Search Report, from PCT/IL05/00812, mailed Feb. 28, 2007.

(56) References Cited

OTHER PUBLICATIONS

International Search Report, from PCT/IB06/052612, mailed Oct. 2, 2007.
Lewis, G., "Properties of Acrylic Bone Cement: State of the Art Review," J. Biomed. Mat. Res. 38(2):155-82 (1997).
Lewis, G., "Toward Standardization of Methods of Determination of Fracture Properties of Acrylic Bone Cement and Statistical Analysis of Test Results," J. Biomed. Mat. Res. 53(6):748-68 (2000).
US Office Action, from U.S. Appl. No. 11/461,072, mailed Jan. 28, 2009.
JP Office Action, from JP Appl No. 2009-517607, mailed Aug. 9, 2011.
Baroud, G., "Influence of Mixing Method on the Cement Temperature—Mixing Time History and Doughing Time of Three Acrylic Cements for Vertebroplasty," Wiley Periodicals Inc. 112-116 (2003).
European Search Report, from EP 10182769.9, mailed Mar. 2, 2011.
European Search Report, from EP 10182693.1, mailed Mar. 2, 2011.
European Search Report, from EP 10192302.7, mailed Mar. 24, 2011.
European Search Report, from EP 10192301.9, mailed Mar. 24, 2011.
European Search Report, from EP 10192300.1, mailed Mar. 24, 2011.
Hide, I. et al., "Percutaneous Vertebroplasty: History, Technique and current Perspectives," Clin. Radiology 59:461-67 (2004).
Hu, M. et al., "Kyphoplasty for Vertebral Compression Fracture Via a Uni-Pedicular Approach," Pain Phys. 8:363-67 (2005).
Liang, B. et al., "Preliminary Clinical Application of Percutaneous Vertebroplasty," Zhong Nan Da Xue Bao Yi Xue Ban 31(1):114-9 (2006).
Noetzel, J. et al., Calcium Phosphate Cements in Medicine and Denistry—A Review of Literature, Schweiz Monatsschr Zehmed 115(12):1148-56 (2005).
Supp. EP Search Report, from EP Appl. No. 07766863.0, dated Apr. 12, 2011.
Amar, Arun P. et al., "Percutaneous Transpedicular Polymethylmethacrylate Vertebroplasty for the Treatment of Spinal Compression Fractures," Neurosurgery 49(5):1105-15 (2001).
Avalione & Baumeister III, Marks' Standard Handbook for Mechanical Engineers, 10 ed, pp. 5-6 (1996).
Barr, J.D., "Percutaneous Vertebroplasty for pain Relief and Spinal Stabilization," Spine 25(8):923-28 (2000).
Belkoff, S. et al., The Biomechanics of Vertebroplasty, the Effect of Cement Volume on Mechanical Behavior, SPINE 26(14):1537-41 (2001).
Belkoff, S.M. et al., "An Ex Vivo Biomechanical Evaluation of a Hydroxyapatite Cement for Use with Kyphoplasty," Am. J. Neurorad. 22:1212-16 (2001).
Belkoff, S.M. et al., "An Ex Vivo Biomechanical Evaluation of a Inflatable Bone Tamp Used in the Treatment of Compression Fracture," SPINE 26(2):151-56 (2001).
Belkoff, S.M. et al., "An In Vitro Biomechanical Evaluation of Bone Cements Used in Percutaneous Vertebroplasty," Bone 25(2):23S-26S (1999).
Blinc, A et al., "Methyl-methacrylate bone cement surface does not promote platelet aggregation or plasma coagulation in vitro," Thrombosis Research 114:179-84 (2004).
Canale et al., "Campbell's operative orthopaedic—vol. 3—ninth ed", Mosby:p. 2097,2121,2184-85,2890-96, (1998).
Codman & Shurtleff, "V-MAX™ Mixing and Delivery Device," Catalog No. 43-1056, 2001.
Combs, S. et al., "The Effects of Barium Sulfate on the Polymerization Temperature and Shear Strength of Surgical Simplex P," Clin. Ortho. and Related Res. pp. 287-291 (Jun. 4, 1979).
Cotton, A. et al., "Percutaneous Vertebroplasty: State of the Art," Scientific Exhibit, Radiographics 18:311-20 (1998).
Dean, J.R. et al., "The Strengthening Effect of Percutaneous Vertebroplasty," Clin Radiol. 55:471-76 (2000).

Deramond, H. et al, "Percutaneous Vertebroplasty with Polymethylmethacrylate, Technique Indications and Results," Radiologic Clinics of North America 36(3) (May 1988).
Deramond, H. et al., "Temperature Elevation Caused by Bone cement Polymerization During Vertbroplasty," Bone 25(2):17S-21S (1999).
DeWijn, J.R., Characterization of Bone Cements, The Institute of Dental Materials Science and Technology and the Dept of Ortho., Catholic University, Netherlands 46:38-51 (1975).
Edeland, "Some additional suggestions for an intervertebral disc prothesis," J. Biomed. Eng. XP008072822, 7(1):57-62 (1985.
European Search Report, from EP09151379.6, mailed Oct. 20, 2009.
European Search Report, from EP06780252.0, mailed Oct. 29, 2009.
Fessler, Richard D. et al., "Vertebroplasty," Neurosurgical Operative Atlas 9:233-240 (2000).
Gangi, A., "CT-Guided Interventional Procedures for Pain Management in the Lumbosacral Spine," Radiographics 18:621-33 (1998).
Gangi, A., "Computed Tomography CT and Fluoroscopy-Guided Vertebroplasty: Results and Complications in 187 Patients," Seminars in Interventional Radiology 16(2):137-42 (1999).
Gangi, A., "Percutaneous Vertebroplasty Guided by a Combination of CT and Fluoroscopy," AJNR 15:83-86 (1994).
Garfin, S. R. et al., "New Technologies in Spine, Kyphoplasty and Vertebroplasty for the Treatment of Painful Osteoporotic Compression Fractures," Spine 26(14:1511-15 (2001).
Grados F. et al.,"Long-Term Observations of Vertebral Osteoporotic Fractures Treated by Percutaneous Vertebroplasty," Rheumatology 39:1410-14 (2000).
Heini, P. et al., "Augmentation of Mechanical Properties in Osteoporatic Vertebral Bones—a Biomechanical Investigation of Vertebroplasty Efficacy With Different Bone Cements," EUR Spine J. v. 10, pp. 164-171, Springer-Verlag (2001).
Heini, P., "Percutaneous Transpedicular Vertebroplasty with PMMA: Operative Technique and Early Results," EUR Spine J. v. 9, pp. 445-450, Springer-Verlag (2000).
Heraeus Palacos R, 2008, Palacos R, high Viscosity Bone Cement.
International Preliminary Report on Patentability, from PCT/IB06/053014, dated Apr. 10, 2008.
International Search Report, from PCT/IL07,00833, mailed Apr. 4, 2008.
International Search Report, from PCT/IL07/00484, mailed Apr. 17, 2008.
Jasper, L.E. et al., "The Effect of Monomer-to-Powder Ratio on the Material Properties of Cranioplastic," Bone 25(2):27S-29S (1999).
Jensen, Mary E. et al., "Percutaneous Polymethylmethacrylate Vertebroplasty in the Treatment of Osteoporotic Vertebral Body Compression Fractures: Technical Aspects," AJNR 18:1897-1904 (1997).
Jensen, Mary E. et al., "Percutaneous Vertebroplasty in the Treatment of Osteoporotic Compression Fractures," Spine Interventions 10(3):547-568 (2000).
Johnson & Johnson Orthopaedics, The CEMVAC Method, Raynham, MA.
Kaufmann et al, "Age of Fracture and Clinical Outcomes of Percutaneous Vertebroplasty," Am. J. Neuroradiology 22:1860-63 (2001).
Kuhn, Klaus-Dieter, Bone Cements—Uptodate Comparison of Physical and Chemical Properties of Commercial Materials, Springer-Verlag Heidelberg Germany p. 7-8, 17, 38 (2000).
Kyphom Medical Professionals, KyphXProducts (Nov. 8, 2001).
Li, C. et al., "Thermal Characterization of PMMA-Based Bone Cement Curing," J. Materials Sci.: Materials in Medicine 15:84-89 (2004).
Lieberman, I.H. et al., "Initial Outcome and Efficacy of Kyphoplasty in the Treatment of Painful Osteoporotic Vertebral Compression Fractures," Spine 26(14:1631-38 (2001).
Mathis, John et al., "Percutaneous Vertebroplasty: A Developing Standard of Care for Vertebral Compression Fractures," AJNR Am. J. Neurorad. 22:373-81 (2001).

(56) References Cited

OTHER PUBLICATIONS

Medsafe Palacos R 2007, Data Sheet : Palacos R Bone cement with Garamycin pp. 1-7; http://www.medsafe.govt.nz/profs/datasheet/p/palacosbonecements.htm.
O'Brien, J. et al., "Vertebroplasty in patients with Severe Vertebral Compression Fractures: A Technical Report," AJNR 21:1555-58 (2000).
Odian, G., "Principles of Polymerization," pp. 20-23, 1991.
Padovani, B. et al., "Pulmonary Embolism Caused by Acrylic Cement: A Rare Complication of Percutaneous Vertebroplasty," AJNR 20:375-77 (1999).
Parallax Medical, Inc., Exflow Cement Delivery System (May 16, 2000).
Rimnac, CM, et al., "The effect of centrifugation on the fracture properties of acrylic bone cements," JB&JS 68A(2):281-87 (1986).
Ryu, K. S. et al., "Dose-Dependent Epidural Leakage of Polymethylmethacrylate after Percutaneous Vertebroplasty in Patients with Osteoporotic Vertebral Compression Fractures," J. Neuro: Spine 96:56-61 (2002).
Shah, T., Radiopaque Polymer Formulations for Medical Devices; Medical Plastics and Biomaterials Special Section; Medical device & Diagnostic Industry pp. 102-111 (2000).
Vasconcelos, C., "Transient Arterial Hypotension Induced by Polymethyacrylated Injection During Percutaneous Vertebroplasty," Letter to the Editor, JVIR (Aug. 2001).
Wimhurst, J.A., et al., "The Effects of Particulate Bone Cements at the Bone-Implant Interface," J. Bone & Joint Surgery pp. 588-592 (2001).
Wimhurst, J.A. et al., "Inflammatory Responses of Human Primary Macrophages to Particulate Bone Cements in Vitro," J. Bone & Joint Surgery 83B:278-82 (2001).
Feldman, H., "Die Geschichte der Injektionen," Laryngo-Rhino-Othol 79:239-46 (2000).
Glasgow Medico-Chirurgical Society, The lancet 1364 (May 18, 1907).
Greenberg, "Filling Root Canals by an Injection Technique," Dental Digest 61-63 (Feb. 1963).
Greenberg, "Filling Root Canals in Deciduous Teeth by an Injection Technique," Dental Digest 574-575 (Dec. 1961).
Greig, D., "A New Syringe for Injecting Paraffin," The Lancet 611-12 (Aug. 29, 1903).
Lake, R., "The Restoration of the Inferior Turbinate Body by Paraffin Injections in the Treatment of Atrophic Rhinitis," The Lancet 168-69 (Jan. 17, 1903).
Paget, S., "The Uses of Paraffin in Plastic Surgery," The Lancet 1354 (May 16, 1903).
Walton, A, "Some Cases of Bone Cavities Treated by Stopping With Paraffin," The Lancet 155 (Jan. 18, 1908).
Cromer, A., "Fluids," Physics for the Life Sciences, 2:136-37 (1977).
JP Office Action, from JP Appl No. 2008-532910, mailed Jul. 19, 2011.
Lindeburg, M., "External Pressurized Liquids," Mechanical Eng. Ref. Manual for the PE Exam, 10:15-14(May 1997).
European Search Report, from EP07827231.7, mailed Sep. 12, 2011.
International Search Report, from corresponding PCT/IL07/01257, dated Jul. 15, 2008.
Japanese Office Action issued Dec. 6, 2011 for Application No. 2008-524651 (9 pages).
Mendizabal et al., Modeling of the curing kinetics of an acrylic bone cement modified with hydroxyapatite. International Journal of Polymeric Materials. 2003;52:927-938.
Morejon et al., Kinetic effect of hydroxyapatite types on the polymerization of acrylic bone cements. International Journal of Polymeric Materials. 2003;52(7):637-654.
Sreeja et al., Studies on poly(methyl methacrylate)/polystyrene copolymers for potential bone cement applications. Metals Materials and Processes. 1996;8(4):315-322.
Yang et al., Polymerization of acrylic bone cement investigated by differential scanning calorimetry: Effects of heating rate and TCP content. Polymer Engineering and Science. Jul. 1997;1182-1187.
Japanese Office Action issued Feb. 21, 2012 for Application No. 2009-516062 (6 pages).
[No Author Listed] Plastic Deformation of Metals and Related Properties. New Age Publishers. p. 1-29.
European Search Report for Application No. 12181745.6, issued Sep. 25, 2012. (9 pages).
Japanese Office Action for Application No. 2009-517607, dated Aug. 28, 2012. (4 pages).
Japanese Office Action for Application No. 2009-516062, dated Oct. 16, 2012 (6 pages).
[No Author Listed] Simplex p. Bone Cement. Stryker Corporation, 2 pages, publication date unknown. Retrieved from <http://www.stryker.com/en-us/products/Orthopaedics/BoneCementSubstitutes/index.htm>.
[No Author Listed] Standard Specification for Acrylic Bone Cement. Designation F 451-08, ASTM International :2008), 11 pages.
Australian Office Action issued Mar. 7, 2013 for Application No. 2012203300 (6 pages).
Chinese Office Action for Application No. 201310064546.9, issued Jul. 31, 2014.
European Communication Issued Jul. 1, 2015 for Application No. 10182769.9, enclosing third party observations ,concerning patentability (Submission dated Jun. 25, 2015) (6 pages).
Notice of Opposition to a European Patent for U.S. Pat. No. 2314259, from KIPA AB (EP Application No. 10182769.9), lated Apr. 28, 2016 (72 pages).
Notice of Opposition to a European Patent for U.S. Pat. No. 2,314,259, from Lover & Abello (EP Application No. 10182769.9), dated Apr. 28, 2016 (40 pages).
European Communication for Application No. 10192301.9, issued Sep. 17, 2015, enclosing third party observations concerning patentability (Submission dated Sep. 11, 2015 (22 pages).
European Search Report for Application No. 13174874.1, issued Nov. 13, 2013 (6 pages).
Extended European Search Report for Application No. 14166420.1, issued Jul. 14, 2014 (9 pages).
Extended European Search Report for Application No. 16173186.4, issued Oct. 6, 2016 (11 pages).
Japanese Office Action issued Apr. 9, 2013 for Application No. 2007-556708.
Japanese Interrogation for Application No. 2009-516062 issued Jul. 9, 2013 (9 pages).
Japanese Office Action for Application No. 2009-517607, dated Aug. 27, 2013. (6 pages).
Japanese Office Action for Application No. 2009-517607, dated Feb. 4, 2014. (8 pages).
Kuehn et al., Acrylic bone cements: composition and properties. Orthop Clin North Am. 2005 Jan;36(1):17-28, v.
Lu Orthopedic Bone Cement. Biomechanics and Biomaterials in Orthopedics. Ed. Poitout London: Springer-Verlag London Limited Jul. 2004 86-88.
Su, W.-F, Polymer Size and Polymer Solutions. Principles of Polymer Design and Synthesis. Chapter 2, pp. 9-26, Springer-Verlag Berlin Heidelberg, 2013.

\* cited by examiner

BONE CEMENT AND METHODS OF USE THEREOF

RELATED APPLICATIONS

The present application claims the benefit under 119(e) of Ser. No. 60/825,609 filed Sep. 14, 2006, the disclosure of which is incorporated herein by reference.

The present application is related to U.S. patent application Ser. No. 11/461,072 filed on Jul. 31, 2006 and entitled "Bone Cement and Methods of Use Thereof", which is a Continuation-in-Part of U.S. application Ser. No. 11/360,251 filed on Feb. 22, 2006, entitled "Methods, Materials and Apparatus for Treating Bone and Other Tissue" and is also a Continuation-in Part of PCT/IL2005/000812 filed on Jul. 31, 2005. The disclosures of these applications are incorporated herein by reference.

The present application is related to PCT application PCT/IL2006/052612 filed on Jul. 31, 2006 and entitled "Bone Cement and Methods of Use thereof" the disclosure of which is incorporated herein by reference.

The present application is also related to a series of U.S. provisional applications entitled "Methods, Materials and Apparatus for Treating Bone and Other Tissue": Ser. No. 60/765,484 filed on Feb. 2, 2006; Ser. No. 60/762,789 filed on Jan. 26, 2006; Ser. No. 60/738,556 filed Nov. 22, 2005; Ser. No. 60/729,505 filed Oct. 25, 2005; Ser. No. 60/720,725 filed on Sep. 28, 2005 and Ser. No. 60/721,094 filed on Sep. 28, 2005. The disclosures of these applications are incorporated herein by reference.

The present application is related to PCT application PCT/IL2006/000239 filed on Feb. 22, 2006; U.S. provisional application Ser. No. 60/763,003, entitled "Cannula" filed on Jan. 26, 2006; U.S. provisional application Ser. No. 60/654,495 entitled "Materials, devices and methods for treating bones". filed Feb. 22, 2005; U.S. Ser. No. 11/194,411 filed Aug. 1, 2005; IL 166017 filed Dec. 28, 2004; IL 160987 filed Mar. 21, 2004; U.S. Provisional Application No. 60/654,784 filed on Jan. 31, 2005; U.S. Provisional Application No. 60/592,149 filed on Jul. 30, 2004; PCT Application No. PCT/IL2004/000527 filed on Jun. 17, 2004, Israel Application No. 160987 filed on Mar. 21, 2004, U.S. Provisional Applications Ser. No.: 60/478,841 filed on Jun. 17, 2003; Ser. No. 60/529,612 filed on Dec. 16, 2003; Ser. No. 60/534,377 filed on Jan. 6, 2004 and Ser. No. 60/554,558 filed on Mar. 18, 2004; U.S. application Ser. No. 09/890,172 filed on Jul. 25, 2001; U.S. application Ser. No. 09/890,318 filed on Jul. 25, 2001 and U.S. application Ser. No. 10/549,409 entitled "Hydraulic Device for the injection of Bone Cement in Percutaneous Vertebroplasty filed on Sep. 14, 2005. The disclosures of all of these applications are incorporated herein by reference.

FIELD OF THE INVENTION

The present invention relates to bone cement, formulations thereof and methods of use thereof.

BACKGROUND OF THE INVENTION

It is common to employ cement to repair bones in a variety of clinical scenarios.

For example, compression fractures of the vertebrae, which are a common occurrence in older persons, cause pain and/or a shortening (or other distortion) of stature. In a procedure known as vertebroplasty cement is injected into a fractured vertebra. Vertebroplasty stabilizes the fracture and reduces pain, although it does not restore the vertebra and person to their original height. In vertebroplasty the cement is typically injected in a liquid phase so that resistance to injection is not too great. Liquid cement may unintentionally be injected outside of the vertebra and/or may migrate out through cracks in the vertebra.

In another procedure, known as kyphoplasty, the fracture is reduced by expanding a device, such as a balloon inside the vertebra and then injecting a fixing material and/or an implant. Kyphoplasty reduces the problem of cement leakage by permitting a lower pressure to be used for injection of the cement.

In general, polymeric cements become more viscous as the polymer chain grows by reacting directly with the double bond of a monomer. Polymerization begins by the "addition mechanism" in which a monomer becomes unstable by reacting with an initiator, a volatile molecule that is most commonly a radical (molecules that contain a single unpaired electron). Radicals bond with monomers, forming monomer radicals that can attack the double bond of the next monomer to propagate the polymer chain. Because radicals are so transient, initiators are often added in the form of an un-reactive peroxide form which is stable in solution. Radicals are formed when heat or light cleaves the peroxide molecule. For applications in which high temperatures are not practical (such as the use of bone cement in vivo), peroxide is typically cleaved by adding a chemical activator such as N,N-dimethyl-p-toluidine. (Nussbaum D A et al: "The Chemistry of Acrylic Bone Cement and Implication for Clinical Use in Image-guided Therapy", J Vasc Interv Radiol (2004); 15:121-126; the content of which is fully incorporated herein by reference).

Examples of commercially available viscous bone cements include, but are not limited to, CMW® Nos. 1, 2 and 3 (DePuy Orthopaedics Inc.; Warsaw, Ind., USA) and Simplex™-P and -RO (Stryker Orthopaedics; Mahwah, N.J., USA). These cements are characterized by a liquid phase after mixing and prior to achieving a viscosity of 500 Pascal-second. In a typical use scenario, these previously available cements are poured, while in a liquid phase, into a delivery device.

There have also been attempts to reduce cement leakage by injecting more viscous cement, for example, during the doughing time and the beginning of polymerization. However, the viscous materials, such as hardening PMMA, typically harden very quickly once they reach a high viscosity. This has generally prevented injection of viscous materials in orthopedic procedures.

Some bone fixing materials, such as polymethylmethacrylate (PMMA), emit heat and possibly toxic materials while setting.

U.S. patents and publication U.S. Pat. Nos. 4,969,888, 5,108,404, 6,383,188, Nos. 2003/0109883, 2002/0068974, U.S. Pat. Nos. 6,348,055, 6,383,190, 4,494,535, 4,653,489 and 4,653,487, the disclosures of which are incorporated herein by reference describe various tools and methods for treating bone.

US patent publication 2004/0260303, the disclosure of which is incorporated herein by reference, teaches an apparatus for delivering bone cement into a vertebra.

Pascual, B., et al., "New Aspects of the Effect of Size and Size Distribution on the Setting Parameters and Mechanical Properties of Acrylic Bone Cements," Biomaterials, 17(5): 509-516 (1996) considers the effect of PMMA bead size on setting parameters of cement. This article is fully incorporated herein by reference.

Hernandez, et al., (2005) "Influence of Powder Particle Size Distribution on Complex Viscosity and Other Properties of Acrylic Bone Cement for Vertebroplasty and Kyphoplasty" Wiley International Science D01:10:1002/jbm.b.30409 (pages 98-103) considers the effect of PMMA bead size distribution on setting parameters of cement. Hernandez suggests that it is advantageous to formulate cement with a liquid phase to facilitate injection. This article is fully incorporated herein by reference.

U.S. Pat. No. 5,276,070 to Arroyo discloses use of acrylic polymers with a molecular weight in the range of 0.5 to 1.5 million Daltons in formulation of bone cement. The disclosure of this patent is fully incorporated herein by reference.

U.S. Pat. No. 5,336,699 to Cooke discloses use of acrylic polymers with a molecular weight of about one hundred thousand Daltons in formulation of bone cement. The disclosure of this patent is fully incorporated herein by reference.

SUMMARY OF THE INVENTION

A broad aspect of the invention relates to a bone cement characterized by a rapid transition from separate liquid monomer and powdered polymer components to a single phase characterized by a high viscosity when the components are mixed together with substantially no intervening liquid phase. Optionally, high viscosity indicates 500 Pascal-second or more. Mixing is deemed complete when 95-100% of the polymer beads are wetted by monomer. In an exemplary embodiment of the invention, mixing is complete in within 60, optionally within 45, optionally within 30 seconds.

In an exemplary embodiment of the invention, the cement is characterized by a working window of several minutes during which the viscosity remains high prior to hardening of the cement. Optionally, viscosity during the working window does not vary to a degree which significantly influences injection parameters. In an exemplary embodiment of the invention, viscosity increases by less than 10% during a sub-window of at least 2 minutes during the working window. Optionally, the viscosity in the working window does not exceed 500, optionally 1,000, optionally 1,500, optionally 2,000 Pascal-second or lesser or greater or intermediate values. In an exemplary embodiment of the invention, the working window lasts 6, optionally 8, optionally 10, optionally 15 minutes or lesser or greater or intermediate times. Optionally, ambient temperature influences a duration of the working window. In an exemplary embodiment of the invention, the cement can be cooled or heated to influence a length of the working window.

An aspect of some embodiments of the invention relates to formulations of bone cement which rely upon two, optionally three or more, sub-populations of polymer beads which are mixed with liquid monomer.

According to exemplary embodiments of the invention, sub-populations may be characterized by average molecular weight (MW) and/or physical size and/or geometry, and/or density. In an exemplary embodiment of the invention, size based and MW based sub-populations are defined independently. In an exemplary embodiment of the invention, the sub-populations are selected to produce desired viscosity characterization and/or polymerization kinetics. Optionally, the polymer beads comprise polymethylmethacrylate (PMMA) and/or a PMMA styrene copolymer. Optionally, PMMA is employed in conjunction with a methylmethacrylate (MMA) monomer.

Optionally, a high molecular weight sub-population contributes to a rapid transition to a high viscosity with substantially no liquid phase. Optionally, a low molecular weight subpopulation contributes to a longer working window.

Optionally, a sub-population with small size contributes to rapid wetting of polymer beads with monomer solution. In an exemplary embodiment of the invention, rapid wetting contributes to a direct transition to a viscous cement with substantially no liquid phase.

In some cases a small percentage of beads may not belong to any relevant sub-population. The small percentage of beads may be, for example 1%, 1.5%,2%, 3%, 4%, 5% or lesser or intermediate or greater percentages.

In one exemplary embodiment of the invention, there are at least two sub-populations of PMMA polymer beads characterized by molecular weights. For example, a first sub-population comprising 95 to 97% (w/w) of the total PMMA beads can be characterized by an average MW of 270,000-300,000 Dalton; a second sub-population (2-3% w/w) can be characterized by an average MW of 3,500,000-4,000,000 Dalton; and a third sub-population (0-3% w/w) can be characterized by an average MW of 10,000-15,000 Dalton.

In an exemplary embodiment of the invention, the polymer beads are characterized by a high surface area per unit weight. Optionally, the beads have a surface area of 0.5 to 1, optionally 0.5 to 0.8 optionally about 0.66 $m^2$/gram or intermediate or lesser or greater values. Optionally, the high surface area/weight ratio improves wetting properties and/or shortens polymerization times, for example by contributing to polymer monomer contact.

In an exemplary embodiment of the invention, a cement characterized by an immediate transition to high viscosity is injected during a working window in a vertebroplasty or kyphoplasty procedure. Optionally, injection is under sufficient pressure to move fractured bone, such as vertebral plates of a collapsed vertebra. Optionally, injection of viscous cement under high pressure contributes to fracture reduction and/or restoration of vertebral height.

In an exemplary embodiment of the invention, the material (e.g., bone cement) includes processed bone (from human or animals origin) and/or synthetic bone. Optionally, the cement has osteoconductive and/or osteoinductive behavior. Additional additives as commonly used in bone cement preparation may optionally be added. These additives include, but are not limited to, barium sulfate and benzoyl peroxide.

According to some embodiments of the invention, a working window length is determined by an interaction between an immediate effect and a late effect. In an exemplary embodiment of the invention, the immediate effect includes MMA solvation and/or encapsulation of PMMA polymer beads. The immediate effect contributes to a high viscosity of the initial mixture resulting from solvation and/or friction between the beads. The late effect is increasing average polymer MW as the beads dissolve and the polymerization reaction proceeds. This increasing average polymer MW keeps viscosity high throughout the working window.

In an exemplary embodiment of the invention, a set of viscosity parameters are used to adjust a cement formulation to produce a cement characterized by a desired working window at a desired viscosity.

In an exemplary embodiment of the invention, there is provided a bone cement comprising an acrylic polymer mixture, the cement characterized in that it achieves a viscosity of at least 500 Pascal-second within 180 seconds following initiation of mixing of a monomer component and a polymer component and characterized by sufficient biocompatibility to permit in-vivo use.

Optionally, the viscosity of the mixture remains between 500 and 2000 Pascal-second for a working window of at least 5 minutes after the initial period.

Optionally, the working window is at least 8 minutes long.

Optionally, the mixture includes PMMA.

Optionally, the mixture includes Barium Sulfate.

Optionally, the PMMA is provided as a PMMA/styrene copolymer.

Optionally, the PMMA is provided as a population of beads divided into at least two sub-populations, each sub-population characterized by an average molecular weight.

Optionally, a largest sub-population of PMMA beads is characterized by an MW of 150,000 Dalton to 300,000 Dalton.

Optionally, a largest sub-population of PMMA beads includes 90-98% (w/w) of the beads.

Optionally, a high molecular weight sub-population of PMMA beads is characterized by an average MW of at least 3,000,000 Dalton.

Optionally, a high molecular weight sub-population of PMMA beads includes 2 to 3% (w/w) of the beads.

Optionally, a low molecular weight sub-population of PMMA beads is characterized by an average MW of less than 15,000 Dalton.

Optionally, a low molecular weight sub-population of PMMA beads includes 0.75 to 1.5% (W/W) of the beads.

Optionally, the PMMA is provided as a population of beads divided into at least two sub-populations, each sub-population characterized by an average bead diameter.

Optionally, at least one bead sub-population characterized by an average diameter is further divided into at least two sub-sub-populations, each sub-sub-population characterized by an average molecular weight.

Optionally, the PMMA is provided as a population of beads divided into at least three sub-populations, each sub-population characterized by an average bead diameter.

Optionally, the cement further includes processed bone and/or synthetic bone.

Optionally, the cement is characterized in that the cement achieves a viscosity of at least 500 Pascal-second when 100% of a polymer component is wetted by a monomer component.

Optionally, the viscosity is at least 800 Pascal-second.

Optionally, the viscosity is at least 1500 Pascal-second.

Optionally, the viscosity is achieved within 2 minutes.

Optionally, the viscosity is achieved within 1 minute.

Optionally, the viscosity is achieved within 45 seconds.

In an exemplary embodiment of the invention, there is provided a bone cement comprising:
a polymer component; and
a monomer component,
wherein, contacting the polymer component and the monomer component produces a mixture which attains a viscosity greater than 200 Pascal-second within 1 minute from onset of mixing and remains below 2000 Pascal-second until at least 6 minutes from onset of mixing.

Optionally, the polymer component comprises an acrylic polymer.

In an exemplary embodiment of the invention, there is provided a particulate mixture formulated for preparation of a bone cement, the mixture comprising:
(a) 60 to 80% polymer beads comprising a main sub-population characterized by an MW of 150,000 Dalton to 300,000 Dalton and a high molecular weight sub-population characterized by an MW of 3,000,000 Dalton to 4,000,000 Dalton; and
(b) 20 to 40% of a material which is non-transparent with respect to X-ray.

Optionally, the polymer beads comprise a third subpopulation characterized by an MW of 10,000 Dalton to 15,000 Dalton.

In an exemplary embodiment of the invention, there is provided a method of making a polymeric bone cement, the method comprising:
(a) defining a viscosity profile including a rapid transition to a working window characterized by a high viscosity;
(b) selecting a polymer component and a monomer component to produce a cement conforming to the viscosity profile; and
(c) mixing the polymer component and a monomer component to produce a cement which conforms to the viscosity profile.

In an exemplary embodiment of the invention, there is provided a cement kit, comprising:
(a) a liquid component including a monomer; and
(b) a powder component including polymeric beads, characterized in that said powder component is provided in a substantially non-normal distribution of at least one of molecular weight of the polymeric beads and size of powder particles such that a cement mixed from the kit has both an increased immediate viscosity and an increased working window as compared to a cement having a substantially normal distribution.

Optionally, the substantially non-normal distribution is a skewed distribution.

Optionally, the substantially non-normal distribution comprises a relatively small component including higher molecular weight beads. Optionally, said component has an average molecular weight of at least a factor of 2 of an average molecular weight of said polymeric beads. Optionally, said factor is at least 3 or is at least 5.

Optionally, the substantially non-normal distribution comprises a relatively small component including smaller sized particles.

BRIEF DESCRIPTION OF THE FIGURES

Exemplary non-limiting embodiments of the invention will be described with reference to the following description of embodiments in conjunction with the figures. Identical structures, elements or parts which appear in more than one figure are generally labeled with a same or similar number in all the figures in which they appear, in which.

DETAILED DESCRIPTION OF EXEMPLARY EMBODIMENTS

Overview of Preparation of Exemplary Bone Cement

Figure 1:
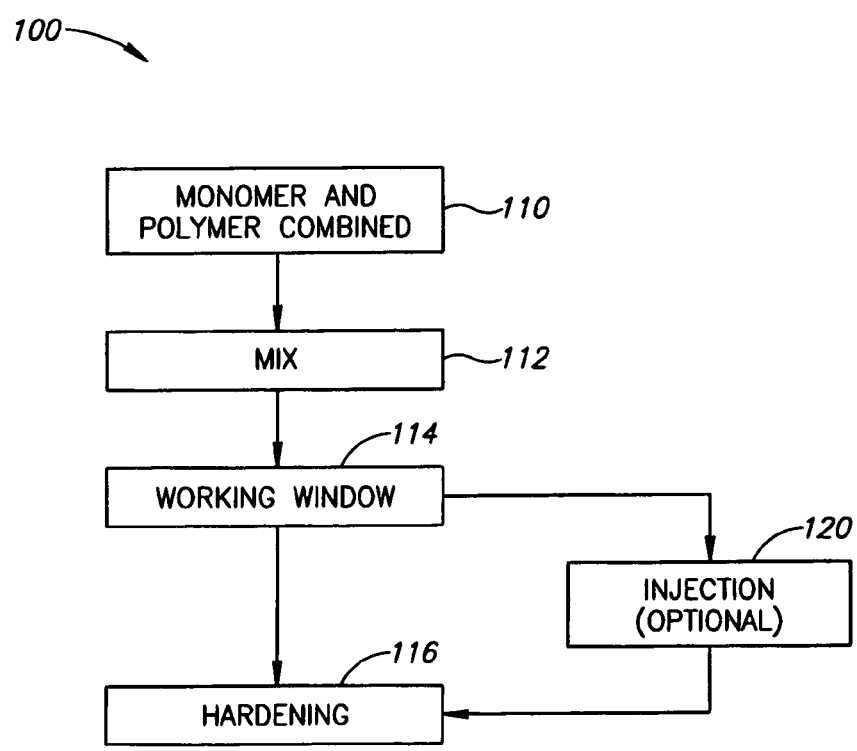
FIG. 1 is a flow diagram illustrating an exemplary method 100 of preparation and behavior of exemplary cements according to the present invention.

FIG. 1 is a flow diagram illustrating preparation and behavior of exemplary cements according to some embodiments of the present invention.

In an exemplary embodiment of the invention, a liquid monomer and a powdered polymer component of a bone cement are combined 110. Optionally, liquid monomer is poured onto powdered polymer.

According to various embodiments of the invention, average polymer molecular weight and/or polymer molecular weight distribution and/or polymer bead size is precisely controlled in order to influence polymerization kinetics and/or cement viscosity. Alternatively or additionally, polymer and/or monomer components may contain ingredients which are not directly involved in the polymerization reaction.

In an exemplary embodiment of the invention, the polymer (e.g. an acrylic polymer such as PMMA) beads are divided into two or more sub-populations. Optionally, the sub populations are defined by molecular weight (MW). In an exemplary embodiment of the invention, the average molecular weight of the acrylic polymer in all the beads is in the range of about 300,000 to 400,000, optionally about 373,000 Dalton. This average MW for all beads was determined experimentally for a batch of beads which produced cement with a desired polymerization profile.

Optionally, the polymer beads are provided as part of an acrylic polymer mixture, for example a mixture including barium sulfate.

At 112 the components are mixed until the polymer is wetted by the monomer. Optionally, when wetting is 95 to 100% complete, the mixture has achieved a desired high viscosity, for example 500 Pascal-second or more. Optionally, mixing 112 is complete within 1, 5, 10, 15, 30, 60, 90, 120 or 180 seconds. In a modern medical facility, it can be advantageous to shorten the mixing time in order to reduce the demand on physical facilities and/or medical personnel. A savings of even 1 to 2 minutes with respect to previously available alternatives can be significant. In an exemplary embodiment of the invention, mixing 112 is conducted in a mixing apparatus of the type described in co-pending application U.S. Ser. No. 11/428,908, the disclosure of which is fully incorporate herein by reference.

After mixing 112 is complete, a working window 114 during which the cement remains viscous but has not fully hardened occurs. According to various exemplary embodiments of the invention, working window 114 may be about 2, 5, 8, 10, 15 or 20 minutes or intermediate or greater times. The duration of the working window may vary with the exact cement formulation and/or ambient conditions (e.g. temperature and/or humidity). Formulation considerations include, but are not limited to polymer MW (average and/or distribution), polymer bead size, concentrations of non-polymerizing ingredient and polymer:monomer ratio.

Working window 114, permits a medical practitioner sufficient time to load a high pressure injection device and inject 120 the cement into a desired location. Optionally, an injection needle or cannula is inserted into the body prior to, or concurrent with mixing 112 so that window 114 need only be long enough for loading and injection 120. Exemplary injection systems are disclosed in co-pending application U.S. Ser. No. 11/360,251 entitled "Methods, materials, and apparatus for treating bone and other tissue" filed Feb. 22, 2006, the disclosure of which is fully incorporated herein by reference.

In an exemplary embodiment of the invention, hardening 116 to a hardened condition occurs after working window 114. The cement hardens 116 even if it has not been injected.

Advantages with Respect to Relevant Medical Procedures

In an exemplary embodiment of the invention, cement with a viscosity profile as described above is useful in vertebral repair, for example in vertebroplasty and/or kyphoplasty procedures.

Optionally, use of cement which is viscous at the time of injection reduces the risk of material leakage and/or infiltrates into the intravertebral cancellous bone (interdigitaion) and/or reduces the fracture [see G Baroud et al, Injection biomechanics of bone cements used in vertebroplasty, Bio-Medical Materials and Engineering 00 (2004) 1-18]. Reduced leakage optionally contributes to increased likelihood of a positive clinical outcome.

In an exemplary embodiment of the invention, the viscosity of the bone cement is 500, optionally 1,000, optionally 1,500, optionally 2,000 Pascal-second or lesser or greater or intermediate values at the time injection begins, optionally 3, 2 or 1 minutes or lesser or intermediate times after mixing 112 begins. Optionally, the viscosity does not exceed 2,000 Pascal-second during working window 114. In an exemplary embodiment of the invention, this viscosity is achieved substantially as soon as 95-100% of the polymer beads are wetted by monomer.

Cement characterized by a high viscosity as described above may optionally be manually manipulated.

In an exemplary embodiment of the invention, cement is sufficiently viscous to move surrounding tissue as it is injected. Optionally, moving of the surrounding tissue contributes to fracture reduction and/or restoration of vertebral height.

An injected volume of cement may vary, depending upon the type and/or number of orthopedic procedures being performed. The volume injected may be, for example, 2-5 cc for a typical vertebral repair and as high as 8-12 cc or higher for repairs of other types of bones. Other volumes may be appropriate, depending for example, on the volume of space and the desired effect of the injection. In some cases, a large volume of viscous cement is loaded into a delivery device and several vertebrae are repaired in a single medical procedure. Optionally, one or more cannulae or needles are employed to perform multiple procedures.

Viscous cements according to exemplary embodiments of the invention may be delivered at a desired flow rate through standard orthopedic cannulae by applying sufficient pressure. Exemplary average injection rates may be in the range of 0.01 to 0.5 ml/sec, optionally about 0.05, about 0.075 or 0.1 ml/sec or lesser or intermediate or greater average flow rates. Optionally, the flow rate varies significantly during an injection period (e.g., pulse injections). Optionally, the flow rate is controlled manually or using electronic or mechanical circuitry. In an exemplary embodiment of the invention, medical personnel view the cement as it is being injected (e.g. via fluoroscopy) and adjust a flow rate and/or delivery volume based upon observed results. Optionally, the flow rate is adjusted and/or controlled to allow a medical practitioner to evaluate progress of the procedure based upon medical images (e.g. fluoroscopy) acquired during the procedure. In an exemplary embodiment of the invention, the cement is sufficiently viscous that advances into the body when pressure is applied above a threshold and ceases to advance when pressure is reduced below a threshold.

Optionally, the threshold varies with one or more of cement viscosity, cannula diameter and cannula length.

Comparison of Exemplary Formulations According to Some Embodiments of the Invention to Previously Available Formulations Although PMMA has been widely used in preparation of bone cement, previously available PMMA based cements were typically characterized by a persistent liquid state after mixing of components.

In sharp contrast, cements according to some exemplary embodiments of the invention are characterized by essentially no liquid state. Optionally, a direct transition from separate polymer and monomer components to a highly viscous state results from the presence of two or more sub-populations of polymer beads.

As a result of formulations based upon bead sub-populations, a viscosity profile of a cement according to an exemplary embodiment of the invention is significantly different from a viscosity profile of a previously available polymer based cement (e.g. PMMA) with a similar average molecular.

Because the viscosity profile of previously available PMMA cements is typically characterized by a rapid transition from high viscosity to fully hardened, these cements are typically injected into bone in a liquid phase so that they do not harden during injection.

In sharp contrast, exemplary cements according to the invention remain highly viscous during a long working window 114 before they harden. This long working window permits performance of a medical procedure of several minutes duration and imparts the advantages of the high viscosity material to the procedure.

It should be noted that while specific examples are described, it is often the case that the formulation will be varied to achieve particular desired mechanical properties. For example, different diagnoses may suggest different material viscosities which may, in turn lead to adjustment of one or more of MW (average and/or distribution), bead size and bead surface area.

In an exemplary embodiment of the invention, the cement is mixed 112 and reaches high viscosity outside the body. Optionally the materials are mixed under vacuum or ventilated. In this manner, some materials with potentially hazardous by-products can be safely mixed and then used in the body.

In an exemplary embodiment of the invention, the cement is formulated so that its mechanical properties match the bone in which it will be injected/implanted. In an exemplary embodiment of the invention, the cement is formulated to mechanically match healthy or osteoporotic trabecular (cancellous) bone. Optionally, the mechanical properties of the bone are measured during access, for example, based on a resistance to advance or using sensors provided through a cannula or by taking samples, or based on x-ray densitometry measurements. In an exemplary embodiment of the invention, strength of the cement varies as a function of one or more of a size of the high MW sub-population and/or a relationship between bead size and bead MW.

In general, PMMA is stronger and has a higher Young modulus than trabecular bone.

For example, healthy Trabecular bone can have a strength of between 1.5-8.0 mega Pascal and a Young modulus of 60-500 mega Pascal. Cortical bone, for example, has strength values of 65-160 mega Pascal and Young modulus of 12-40 giga Pascal. PMMA typically has values about half of Cortical bone (70-120 mega Pascal strength).

Figure 2:
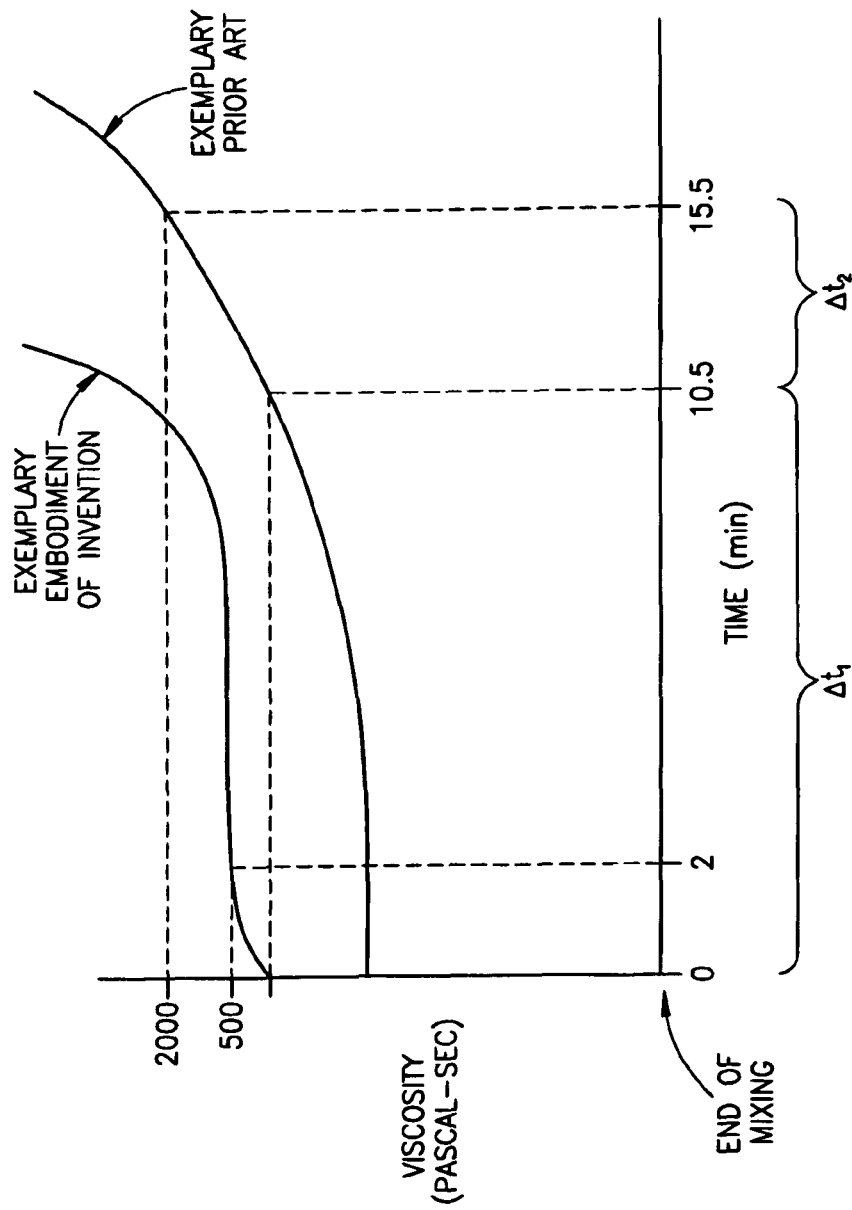
FIG. 2 is a graph of viscosity profiles depicting viscosity (Pascal-second) as a function of time (minutes) for an exemplary cement according to the invention and an exemplary prior art cement.

FIG. 2 is a plot of viscosity as a function of time for an exemplary bone cement according to the present invention. The figure is not drawn to scale and is provided to illustrate the principles of exemplary embodiments of the invention. The end of a mixing process is denoted as time 0. Mixing is deemed to end when 95-100% of acrylic polymer beads have been wetted with monomer. The graph illustrates an exemplary bone cement which enters a high viscosity plastic phase upon mixing so that it has substantially no liquid phase.

FIG. 2 illustrates that once a high viscosity is achieved, the viscosity remains relatively stable for 2, optionally 5, optionally 8 minutes or more. In an exemplary embodiment of the invention, this interval of stable viscosity provides a working window 114 (indicated here as $\Delta t_1$) for performance of a medical procedure. In an exemplary embodiment of the invention, stable viscosity means that the viscosity of the cement changes by less than 200 Pascal-second during a window of at least 2 minutes optionally at least 4 minutes after mixing is complete. Optionally, the window begins 1, 2, 3, 4 or 5 minutes after mixing begins or lesser or intermediate times. In an exemplary embodiment of the invention, the viscosity of the cement remains below 1500, optionally 2000 Pascal-second for at least 4, optionally at least 6, optionally at least 8, optionally at least 10 minutes or intermediate or greater times from onset of mixing.

For purposes of comparison, the graph illustrates that an exemplary prior art cement reaches a viscosity comparable to that achieved by an exemplary cement according to the invention at time zero at a time of approximately 10.5 minutes post mixing and is completely set by about 15.5 minutes ($\Delta t_2$).

A working window 114 during which viscosity is between 400 and 2000 Pascal-second for an exemplary cement according to some embodiments of the invention ($\Delta t_1$) is both longer and earlier than a comparable window for an exemplary prior art cement ($\Delta t_2$). Optionally, ($\Delta t_1$) begins substantially as soon as mixing is complete.

Exemplary Cement Formulations

According to various exemplary embodiments of the invention, changes in the ratios between a powdered polymer component and a liquid monomer component can effect the duration of working window 114 and/or a viscosity of the cement during that window. Optionally, these ratios are adjusted to achieve desired results.

In an exemplary embodiment of the invention, the powdered polymer component contains PMMA (69.3% w/w); Barium sulfate (30.07% w/w) and Benzoyl peroxide (0.54% w/w).

In an exemplary embodiment of the invention, the liquid monomer component contains MMA (98.5% v/v); N, N-dimethyl-p-toluidine (DMPT) (1.5% v/v) and Hydroquinone (20 ppm).

In a first exemplary embodiment of the invention, 20±0.3 grams of polymer powder and 9±0.3 grams of liquid monomer are combined (weight ratio of ~2.2:1).

In a second exemplary embodiment of the invention, 20±0.3 grams of polymer powder and 8±0.3 grams of liquid are combined (weight ratio of 2.5:1).

Under same weight ratio of second exemplary embodiment (2.5:1), a third exemplary embodiment may include a combination of 22.5±0.3 grams of polymer powder and 9±0.3 grams of liquid.

In general, increasing the weight ratio of polymer to monomer produces a cement which reaches a higher viscosity in less time. However, there is a limit beyond which there is not sufficient monomer to wet all of the polymer beads.

Optionally the powdered polymer component may vary in composition and contain PMMA (67-77%, optionally 67.5-71.5% w/w); Barium sulfate (25-35%; optionally 28-32% w/w) and Benzoyl peroxide (0.4-0.6% w/w) and still behave substantially as the powder component recipe set forth above.

Optionally the liquid monomer component may vary in composition and contain Hydroquinone (1-30 ppm; optionally 20-25 ppm) and still behave substantially as the liquid component recipe set forth above.

Viscosity Measurements Over Time for Exemplary Cements

In order to evaluate the viscosity profile of different exemplary batches of cement according to some embodiments of the invention, a bulk of pre-mixed bone cement is placed inside a Stainless Steel injector body. Krause et al. described a method for calculating viscosity in terms of applied force. ("The viscosity of acrylic bone cements", Journal of Biomedical Materials Research, (1982): 16:219-243). This article is fully incorporated herein by reference.

In the experimental apparatus an inner diameter of the injector body is approximately 18 mm. A distal cylindrical outlet has an inner diameter of approximately 3 mm and a length of more than 4 mm. This configuration simulates a connection to standard bone cement delivery cannula/bone access needle. A piston applies force (F), thus causing the bone cement to flow through the outlet. The piston is set to move with constant velocity of approximately 3 mm/min. As a result, piston deflection is indicative of elapsed time.

The experimental procedure serves as a kind of capillary extrusion rheometer. The rheometer measures the pressure difference from an end to end of the capillary tube. The device is made of an 18 mm cylindrical reservoir and a piston. The distal end of the reservoir consist of 4 mm long 3 mm diameter hole. This procedure employs a small diameter needle and high pressure. Assuming steady flow, isothermal conditions and incompressibility of the tested material, the viscous force resisting the motion of the fluid in the capillary is equal to the applied force acting on the piston measured by a load cell and friction. Results are presented as force vs. displacement. As displacement rate was constant and set to 3 mm/min, the shear rate was constant as well. In order to measure the time elapses from test beginning, the displacement rate is divided by 3 (jog speed).

Figure 3:
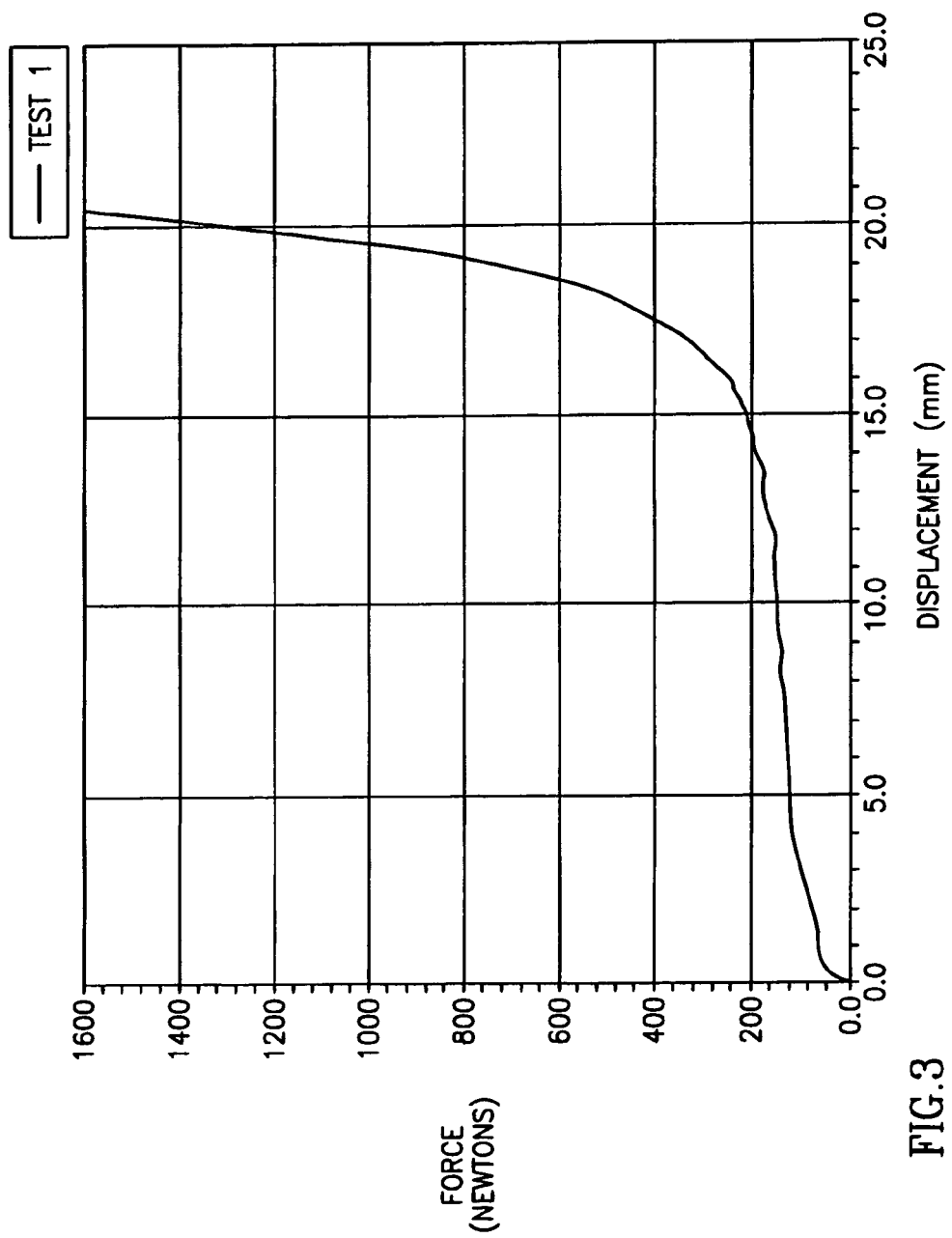
FIGS. 3 and 4 are graphs indicating viscosity as Newtons of applied force per unit displacement (mm) under defined conditions for exemplary cements according to the invention and illustrate the time window for injection which is both early and long.

FIG. 3 indicates a viscosity profile of a first exemplary batch of cement according to the invention as force (Newtons) vs. displacement (mm). The cement used in this experiment included a liquid component and a powder component as described above in "Exemplary cement formulations".

In this test (Average temperature: 22.3° C.; Relative Humidity: app. 48%) the cement was mixed for 30-60 seconds, then manipulated by hand and placed inside the injector. Force was applied via the piston approximately 150 seconds after end of mixing, and measurements of force and piston deflection were taken.

At a time of 2.5 minutes after mixing (0 mm deflection) the force applied was higher than 30 N.

At a time of 6.5 minutes after mixing (12 mm deflection) the force applied was about 150 N.

At a time of 7.5 minutes after mixing (15 mm deflection) the force applied was higher than 200 N.

At a time of 8.5 minutes after mixing (18 mm deflection) the force applied was higher than 500 N.

At a time of 9.17 minutes after mixing (20 mm deflection) the force applied was higher than 1300 N.

Figure 4:
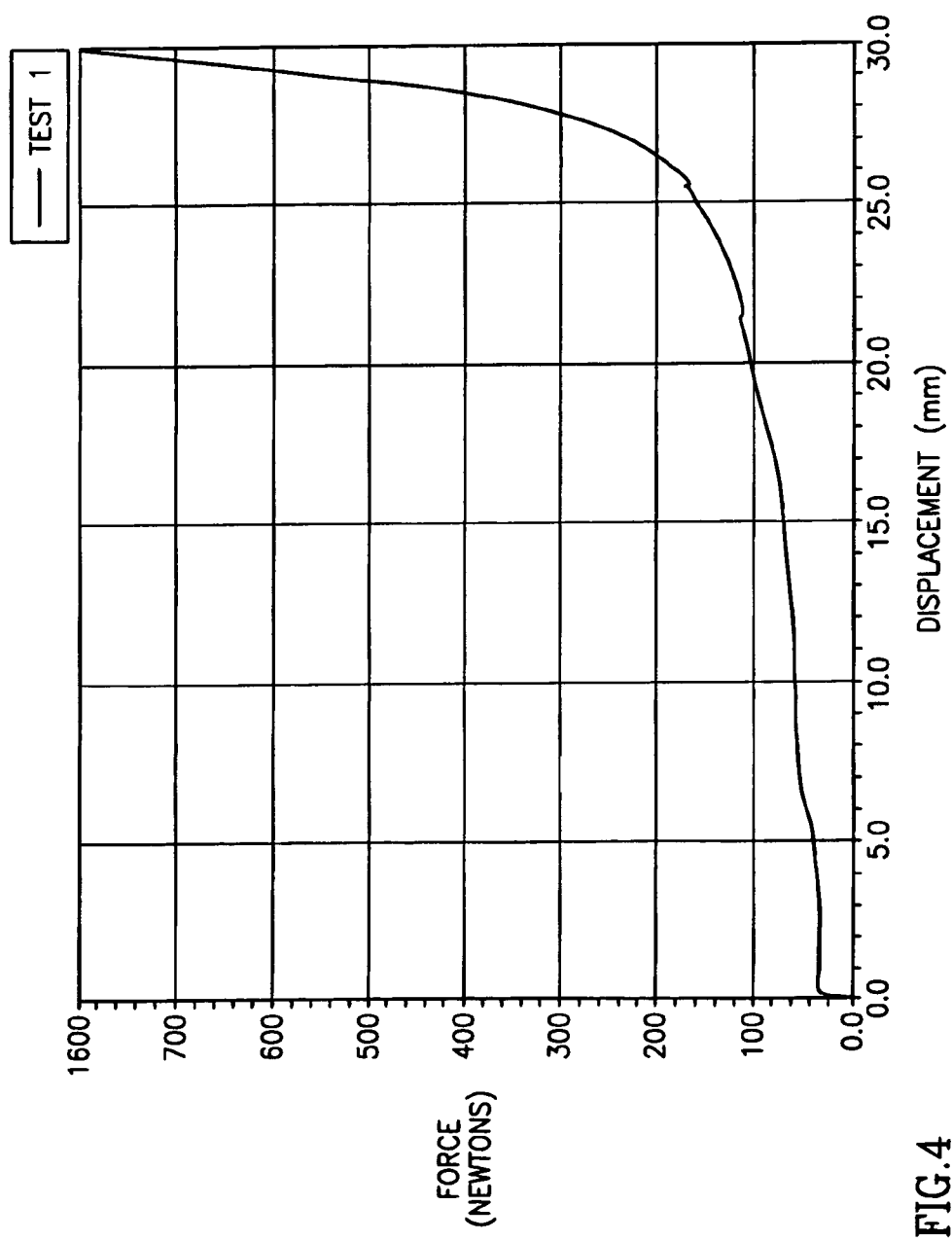

FIG. 4 indicates a viscosity profile of an additional exemplary batch of cement according to the invention as force (Newtons) vs. displacement (mm). The cement in this test was prepared according to the same formula described for the experiment of FIG. 3. In this test (Average 21.1° C.; Relative Humidity: app. 43%) the cement was mixed for approximately 45 seconds, then manipulated by hand and placed inside the injector. Force was applied via piston approximately 150 seconds after end of mixing, and measurements of force and piston deflection were taken.

At a time of 2.25 minutes after mixing (0 mm deflection) the force applied was higher than 30 N.

At a time of 8.25 minutes after mixing (18 mm deflection) the force applied was about 90 N.

At a time of 10.3 minutes after mixing (25 mm deflection) the force applied was higher than 150 N.

At a time of 11.4 minutes after mixing (28.5 mm deflection) the force applied was higher than 500 N.

At a time of 12.25 minutes after mixing (30 mm deflection) the force applied was higher than 800 N.

Results shown in FIGS. 3 and 4 and summarized hereinabove illustrate that exemplary bone cements according to some embodiments the invention achieve high viscosity in 2.25 minutes or less after mixing is completed. Alternatively or additionally, these cements are characterized by short mixing time (i.e. transition to highly viscous plastic phase in 30 to 60 seconds). The exemplary cements provide a "working window" for injection of 4.5 to 6.3 minutes, optionally longer if more pressure is applied and/or ambient temperatures are lower. These times correspond to delivery volumes of 14.9 and 20.8 ml respectively (vertebroplasty of a single vertebra typically requires about 5 ml of cement). These volumes are sufficient for most vertebral repair procedures. These results comply with the desired characteristics described in FIG. 2. Differences between the two experiments may reflect the influence of temperature and humidity on reaction kinetics.

Molecular Weight Distribution

In an exemplary embodiment of the invention, the average molecular weight (MW) is skewed by the presence of one or more small sub-population of beads with a molecular weight which is significantly different from a main sub-population of polymer beads. The one or more small sub-population of beads may have a MW which is significantly higher and/or significantly lower than the average MW.

In an exemplary embodiment of the invention, the presence of even a relatively small sub-population of polymer beads with a MW significantly above the average MW causes the cement to achieve a high viscosity in a short time after wetting of polymer beads with monomer solution. Optionally, increasing a size of the high MW sub-population increases the achieved viscosity. Alternatively or additionally, increasing an average MW of the high MW sub-population increases the achieved viscosity and/or decreases the time to reach high viscosity.

Optionally, the one or more small sub-population of beads are provided in a formulation in which, the average molecular weight of PMMA in all beads is 80,000, optionally 100,000, optionally 120,000, optionally 140,000, optionally 160,000, optionally 180,000, optionally, 250,000, optionally 325,000, optionally 375.000, optionally 400,000, optionally 500,000 Dalton or intermediate or lesser or greater values.

In another exemplary embodiment of the invention, the average molecular weight of the acrylic polymer in the beads is in the range of about 130,000 to 170,000, optionally about 160,000 Dalton.

In an exemplary embodiment of the invention, a main sub-population of PMMA beads has a MW of about 150,000 Dalton to about 500,000 Dalton, optionally about 250,000 Dalton to about 300,000 Dalton, optionally about 275,000 Dalton to about 280,000 Dalton. Optionally, about 90-98% [w/w], optionally about 93% to 98%, optionally about 95% to 97% of the beads belong to the main sub-population.

In an exemplary embodiment of the invention, a second high MW sub-population of PMMA beads has a MW of about 600,000 Dalton, to about 5,000,000 Dalton, optionally about 3,000,000 Dalton to about 4,000,000 Dalton, Optionally about 3,500,000 Dalton to about 3,900,000 Dalton. Optionally, approximately 0.25% to 5% [w/w], optionally about 1% to 4%, optionally about 2% to 3% of the beads belong to this high MW sub-population. Optionally, this high molecular weight sub-population comprises a styrene co-polymer. In an exemplary embodiment of the invention, a higher molecular weight in this sub-population of beads contributes to a high viscosity within 2, optionally within 1, optionally within 0.5 minutes or less of wetting of polymer beads with monomer solution.

In an exemplary embodiment of the invention, a third low MW sub-population of PMMA beads has a MW in the range of about 1,000 Dalton to about 75,000 Dalton, optionally about 10,000 Dalton to about 15,000 Dalton, optionally about 11,000 Dalton to about 13,000 Dalton. Optionally, approximately 0.5 to 2.0% [w/w], optionally about 1% of the beads belong to this sub-population.

Optionally the MW sub-populations are distinct from one another. This can cause gaps between sub-populations with respect to one or more parameters. In an exemplary embodiment of the invention, the sub-populations are represented as distinct peaks in a chromatographic separation process. Optionally, the peaks are separated by a return to baseline. Depending upon the sensitivity of detection, a background level of noise may be present. Optionally, gaps are measured relative to the noise level.

Optionally the sub-populations abut one another so that no gaps are apparent. In an exemplary embodiment of the invention, the sub-populations are represented as overlapping peaks in a chromatographic separation process. In this case, there is no return to baseline between the peaks.

Experimental Analysis of an Exemplary Batch of Cement

Sub-populations characterized by an average molecular weight were identified and quantitated using chromatographic techniques known in the art. Exemplary results described herein are based upon GPC analysis. Each peak in the GPC analysis is considered a sub-population. Similar analyses may be conducted using HPLC. Results are summarized in table 1.

TABLE I

MW distribution of polymer beads based upon GPC analysis of a bone cement according to the powdered polymer component described in "Exemplary cement formulations" hereinabove.

| Fraction | % of total | PDI[1] | Mw[2] | Mn[3] |
|---|---|---|---|---|
| 1 | 96.5 | 1.957 | 278,986 | 142,547 |
| 2 | 2.5 | 1.048 | 3,781,414 | 3,608,941 |
| 3 | 1.0 | 1.009 | 12,357 | 12,245 |
|  | 100.0 | 2.955 | 373,046 | 126,248 |

[1]polydispersity index (PDI), is a measure of the distribution of molecular weights in a given polymer sample and is equal to MW/Mn.
[2]MW is the weight average molecular weight in Daltons
[3]Mn is the number average molecular weight in Daltons Table I illustrates an exemplary embodiment of the invention with three sub-populations of acrylic polymer beads.

The main sub-population (fraction 1) of PMMA beads has a molecular weight (MW) of 278,986 Dalton. About 96.5% of the beads belong to this sub-population.

A second sub-population (fraction 2) of PMMA beads has MW of 3,781,414 Dalton. Approximately 2.5% of the beads belong to this sub-population.

A third sub-population of PMMA beads (fraction 3) has an MW of 12,357 Dalton. Approximately 1% of the beads belong to this sub-population.

In an exemplary embodiment of the invention, cement comprising these three sub-populations is characterized by a short mixing time and/or achieves a viscosity of 500 to 900 Pascal-second in 0.5 to 3, optionally 0.5 to 1.5 minutes from the beginning of mixing and/or which remains below 2000 Pascal-second for at least 6 to 10 minutes after mixing. A short mixing time followed by a long working window is considered advantageous in orthopedic procedures where operating room availability and medical staff are at a premium.

Size Distribution

In an exemplary embodiment of the invention, the bone cement is characterized by beads with a size distribution including at least two sub-populations of polymer beads.

In an exemplary embodiment of the invention, polymer bead diameter is in the range of 10-250 microns, with a mean value of approximately 25, 30, 40, 50, 60 microns, or a lower or a higher or an intermediate diameter. In an exemplary embodiment of the invention, sub-populations of beads are defined by their size.

Optionally, a main sub-population of polymer (e.g. PMMA) beads is characterized by a diameter of about 20 to about 150, optionally about 25 to about 35, optionally an average of about 30 microns. Beads in this main sub-population are optionally far smaller than the smallest beads employed by Hernandez et al. (2005; as cited above). Presence of small beads can contribute to a rapid increase in viscosity after wetting with monomer.

Optionally a second sub-population of large polymer beads is characterized by a diameter of about 150 microns or more. Presence of large beads can slow down the polymerization reaction and prevent hardening, contributing to a long working window.

Optionally, the remaining beads are characterized by a very small average diameter, for example less than 20, optionally less than 15, optionally about 10 microns or less. Presence of very small beads can facilitate rapid wetting with monomer liquid during mixing and contribute to a fast transition to a viscous state with substantially no liquid phase.

Microscopic analysis indicates that the beads are typically spherical or spheroid.

Hernandez et al. (2005; as cited above) examined the possibility of adjusting the average polymer bead size by combining two types of beads with average sizes of 118.4μ (Colacry) and 69.7μ (Plexigum) together in different ratios. However, Hernandez's goal was a formulation which is "liquid enough to be injected". All formulations described by Hernandez are characterized by an increase in viscosity from 500 Pascal-sec to 2000 Pascal-sec in about two minutes or less (corresponds to window 114). Hernandez does not hint or suggest that there is any necessity or advantage to increasing the size of this window.

Microscopic analysis also indicated that the barium sulfate particles are present as elongate amorphous masses with a length of approximately 1 micron. In some cases aggregates of up to 70 microns in size were observed. In some cases, barium sulfate particles and polymer beads aggregated together. Optionally, aggregates of Barium sulfate and polymer beads can delay wetting of polymer beads by monomer.

In an exemplary embodiment of the invention, MMA solvates and/or encapsulates the PMMA polymer beads and the viscosity of the initial mixture is high due to the solvation and/or friction between the beads. As the beads dissolve viscosity remains high due to polymerization which increases the average polymer MW.

The following table II shows an exemplary particle size distribution, for example, one suitable for the cement of Table I, based on an analysis of particles within the ranges of 0.375-2000 microns:

TABLE II

Particles size distribution of an exemplary powdered component

| Vol. % | 10 | 25 | 50 | 75 | 90 |
|---|---|---|---|---|---|
| Max Beads Diameter [microns] | 2.3 | 25.75 | 45.07 | 60.68 | 76.34 |

Experimental Analysis of a Second Exemplary Batch of Cement

Another example of a cement kit for mixture includes a liquid and a powder, which includes a mass of acrylic polymer beads. This cement kit is formulated as follows:
(a) liquid (9.2 gr)
 (i) Methylmethacrylate (MMA) 98.5% (vol)
 (ii) N,N-dimethyl-p-toluidine 1.5% (vol)
 (iii) Hydroquinone 20 ppm (vol)
(b) powder (20 gr)
 (i) Polymethylmethacrylate (PMMA) 69.39% (weight)
 (ii) Barium Sulfate 30.07% (weight)
 (iii) Benzoyl Peroxide 0.54% (weight)

As noted above, in other formulations the amounts may be varied, for example, to achieve specific mechanical (or other) properties, or they may be varied and achieve same mechanical properties. In another variation, medication may be added to the powder and/or liquid phases. Other liquid phases may be used as well, for example, as known in the art for PMMA-type cements. The ratios may be varied, for example, as described above.

Table III summarizes a molecular weight distribution of the acrylic bead component of this exemplary cement. It is hypothesized that providing a non-normal distribution of molecular weights with a heavier molecular weight component (e.g., by skewing the MW distribution by including relatively higher molecular weight beads) provides an increased immediate viscosity. In an exemplary embodiment of the invention, the higher MW beads are in a relatively small amount (for example, less than 20%, less than 10%, less than 5%) and have a MW of between 500,000 to 2,000,000 Dalton, optionally 600,000 to 1,200,000 Dalton (for example as shown in the table below).

TABLE III

MW distribution of polymer beads of a bone cement of the second exemplary batch

| Range of Molecular Weights [Dalton] | % of total |
|---|---|
| 1,000,000-2,000,000 | 0.38% |
| 500,000-1,000,000 | 3.6% |

TABLE III-continued

MW distribution of polymer beads of a bone cement of the second exemplary batch

| Range of Molecular Weights [Dalton] | % of total |
|---|---|
| 250,000-500,000 | 12.4% |
| 100,000-250,000 | 36.4% |
| 50,000-100,000 | 26.6% |
| 25,000-50,000 | 14.2% |
| 10,000-25,000 | 5.3% |
| 8,000-10,000 | 0.5% |
| 5,000-8,000 | 0.4% |

In an exemplary embodiment of the invention, the bone cement is characterized by beads with a size distribution including at least two sub-populations of different materials. Optionally, at least two sub-populations include polymer (e.g. PMMA) beads and Barium Sulfate particles. Optionally, the range of particles diameter of the Barium Sulfate is 0.01-15 microns, optionally 0.3 to 3 microns, optionally with an average of about 0.5 microns or lesser or intermediate or greater sizes.

In an exemplary embodiment of the invention, polymer bead diameter is in the range of 10-250 microns, optionally. 15-150 microns, with a mean value of approximately 25, 30, 40, 50, 60 microns. Lower or a higher or intermediate diameters are possible as well, for example, based on the setting considerations described above. In some cases, large particle sizes, for example, particles having diameters exceeding 120 microns (e.g., when the average diameter is on the order of 60 microns) are the result of Barium sulfate primary particle aggregation on PMMA particle beads.

An exemplary distribution of bead sizes for the exemplary cement of table III, based on an analysis of particles within the range of 0.04-2000 microns, is described in Table IV:

TABLE IV

Particles size distribution of a second exemplary powdered component of bone cement

| Vol. % | 10 | 25 | 50 | 75 | 90 |
|---|---|---|---|---|---|
| Max Beads Diameter [microns] | 2 | 9 | 46.5 | 70.7 | 90.5 |

Figure 5:
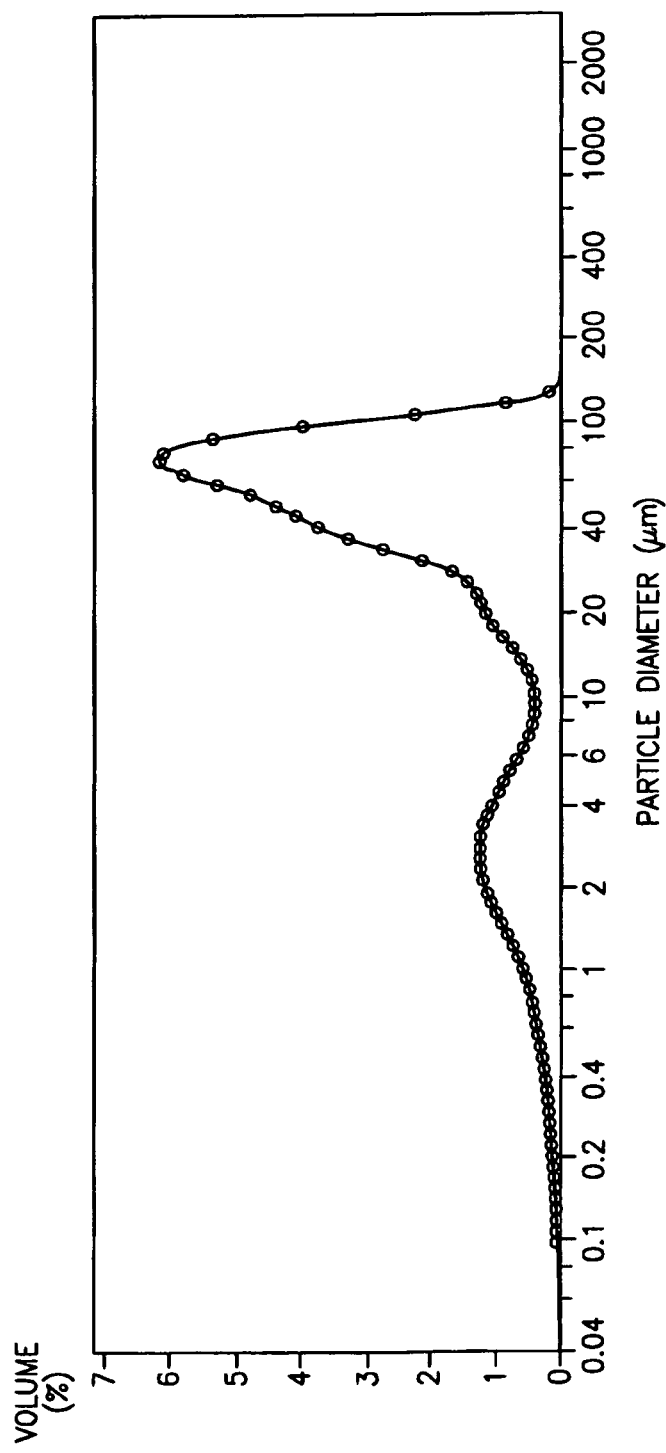
FIG. 5 is a graph showing the results of bead size distribution analysis, for a bead formulation in accordance with an exemplary embodiment of the invention.

FIG. 5 is a graph which visually shows the values of table IV

Size and MW are Independent Variables

In an exemplary embodiment of the invention, size based and MW based sub-populations are determined independently. For example, MW may be determined chromatographically and size may be determined by microscopic analysis. As a result, beads classed in a single size sub-population may be classed in two or more MW sub-populations and/or beads classed in a single MW sub-population may be classed in two or more size sub-populations.

Mechanical Viscosity Increasing Agents

In an exemplary embodiment of the invention, the cement includes particles characterized by a large surface which do not participate in the polymerization reaction. The large surface area particles can impart added viscosity to the cement mixture independent of polymerization. Optionally, the added viscosity comes from friction of particles against one another in the cement.

Examples of materials which do not participate in the polymerization reaction but increase viscosity include, but are not limited to Zirconium, hardened acrylic polymer, barium sulfate and bone.

Optionally, materials which do not participate in the polymerization reaction but increase viscosity can at least partially substitute for high MW polymers in influencing a viscosity profile.

Desired Polymerization Reaction Kinetics

In an exemplary embodiment of the invention, mixture of polymer and monomer produces a high viscosity mixture with substantially no intervening liquid phase within 180, optionally within 120, optionally within 100, optionally within 60, optionally within 30, optionally within 15 seconds or greater or intermediate times from onset of mixing.

In an exemplary embodiment of the invention, once a high viscosity is achieved, the viscosity remains stable for 5 minutes, optionally 8 minutes, optionally 10 minutes or lesser or intermediate or greater times. Optionally, stable viscosity indicates a change of 10% or less in two minutes and/or a change of 20% or less in 8 minutes. The time during which viscosity is stable provides a working window for performance of a medical procedure.

These desired reaction kinetics can be achieved by adjusting one or more of average polymer MW, polymer MW distribution, polymer to monomer ratio and polymer bead size and/or size distribution.

General Considerations

In an exemplary embodiment of the invention, a powdered polymer component and a liquid monomer component are provided as a kit. Optionally, the kit includes instructions for use. Optionally, the instructions for use specify different proportions of powder and liquid for different desired polymerization reaction kinetics.

In an exemplary embodiment of the invention, a bone cement kit including at least two, optionally three or more separately packaged sub-populations of beads and a monomer liquid is provided. Optionally, the kit includes a table which provides formulations based on combinations of different amounts of bead sub-populations and monomer to achieve desired properties.

It is common practice in formulation of acrylic polymer cements to include an initiator (e.g. benzoyl peroxide; BPO) in the powdered polymer component and/or a chemical activator (e.g. DMPT) into the liquid monomer component. These components can optionally be added to formulations according to exemplary embodiments of the invention without detracting from the desired properties of the cement.

Optionally, an easily oxidized molecule (e.g. hydroquinone) is added to the liquid component to prevent spontaneous polymerization during storage (stabilizer). The hydroquinone can be oxidized during storage.

Optionally, cement may be rendered radio-opaque, for example by adding a radio-opaque material such as barium sulfate and/or zirconium compounds and/or bone (e.g. chips or powder) to the powder and/or liquid component.

While the above description has focused on the spine, other tissue can be treated as well, for example, compacted tibia plate and other bones with compression fractures and for fixation of implants, for example, hip implants or other bone implants that loosened, or during implantation. Optionally, for tightening an existing implant, a small hole is drilled to a location where there is a void in the bone and material is extruded into the void.

It should be noted that while use of the disclosed material as bone cement is described, non-bone tissue may optionally be treated. For example, cartilage or soft tissue in need of tightening may be injected with a high viscosity polymeric mixture. Optionally, the delivered material includes an encapsulated pharmaceutical and is used as a matrix to slowly release the pharmaceutical over time. Optionally, this is used as a means to provide anti-arthritis drugs to a joint, by forming a void and implanting an eluting material near the joint.

It should be noted that while use of PMMA has been described, a wide variety of materials can be suitable for use in formulating cements with viscosity characteristics as described above. Optionally, other polymers could be employed by considering polymer molecular weight (average and/or distribution) and/or bead size as described above. Optionally, at least some of the beads include styrene. In an exemplary embodiment of the invention, styrene is added to MMA beads in a volumetric ratio of 5-25%. Optionally, addition of styrene increases creep resistance.

According to various embodiments of the invention, a bone cement according to the invention is injected into a bone void as a preventive therapy and/or as a treatment for a fracture, deformity, deficiency or other abnormality. Optionally, the bone is a vertebral body and/or a long bone. In an exemplary embodiment of the invention, the cement is inserted into the medullary canal of a long bone. Optionally, the cement is molded into a rod prior to or during placement into the bone. In an exemplary embodiment of the invention, the rod serves as an intra-medular nail.

Exemplary Characterization Tools

Molecular weight and polydispersity can be analyzed, for example by Gel permeation chromatography(GPC) system (e.g. Waters 1515 isocratic HPLC pump with a Waters 2410 refractive-index detector and a Rheodyne (Coatati, Calif.) injection valve with a 20-µL loop (Waters Mass.)). Elution of samples with $CHCl_3$ through a linear Ultrastyragel column (Waters; 500-Å pore size) at a flow rate of 1 ml/min provides satisfactory results.

It will be appreciated that various tradeoffs may be desirable, for example, between available injection force, viscosity, degree of resistance and forces that can be withstood (e.g. by bone or injection tools). In addition, a multiplicity of various features, both of method and of cement formulation have been described. It should be appreciated that different features may be combined in different ways. In particular, not all the features shown above in a particular embodiment are necessary in every similar exemplary embodiment of the invention. Further, combinations of the above features are also considered to be within the scope of some exemplary embodiments of the invention. In addition, some of the features of the invention described herein may be adapted for use with prior art devices, in accordance with other exemplary embodiments of the invention.

Section headers are provided only to assist in navigating the application and should not be construed as necessarily limiting the contents described in a certain section, to that section. Measurements are provided to serve only as exemplary measurements for particular cases, the exact measurements applied will vary depending on the application. When used in the following claims, the terms "comprises", "comprising", "includes", "including" or the like means "including but not limited to".

It will be appreciated by a person skilled in the art that the present invention is not limited by what has thus far been described. Rather, the scope of the present invention is limited only by the following claims.

The invention claimed is:

1. A cement kit, comprising:
   (a) a liquid component including a monomer; and
   (b) a powder component including polymeric beads,
   in which the distribution of the molecular weight of the powder component is non-normal so that it is skewed to a higher molecular weight by introduction of higher molecular weight beads, the non-normal distribution of the molecular weight of the powder component causing (a) an increase in the immediate viscosity of a mixture of the liquid and powder components and compared with a cement having a substantially normal distribution, and (b) an increase in the length of the working window period in which the viscosity of the cement does not exceed 500 Pa.s compared with a cement having a substantially normal distribution.

2. A cement kit according to claim 1, in which the higher molecular weight beads have an average molecular weight of at least a factor of 2 of an average molecular weight of the polymeric beads.

3. A cement kit according to claim 2, in which the factor is at least 3.

4. A cement kit according to claim 3, in which the factor is at least 5.

5. A cement kit according to claim 1, further comprising a relatively small component including smaller sized beads.

6. A cement kit according to claim 1, wherein the polymeric beads comprise PMMA.

7. A cement kit according to claim 1, wherein the higher molecular weight beads have a molecular weight of about 600,000 Dalton to about 5,000,000 Dalton.

8. A cement kit according to claim 1, wherein the higher molecular weight beads have a molecular weight of about 3,000,000 to 4,000,000 Dalton.

9. A cement kit according to claim 1, wherein the higher molecular weight beads have a molecular weight of about 3,500,000 to 3,900,000 Dalton.

10. A cement kit according to claim 1, wherein an average molecular weight of the polymeric beads is about 130,000 to 170,000 Dalton.

11. A cement kit according to claim 1, wherein an average molecular weight of the polymeric beads is about 375,000 Dalton.

* * * * *